(12) United States Patent
Bankiewicz et al.

(10) Patent No.: US 10,426,374 B2
(45) Date of Patent: *Oct. 1, 2019

(54) METHODS FOR BIOMEDICAL TARGETING AND DELIVERY AND DEVICES AND SYSTEMS FOR PRACTICING THE SAME

(71) Applicant: The Regents of the University of California, Oakland, CA (US)

(72) Inventors: Krystof S. Bankiewicz, Oakland, CA (US); Kathryn H. Rosenbluth, San Francisco, CA (US); Adrian P Kells, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/039,044

(22) Filed: Jul. 18, 2018

(65) Prior Publication Data

US 2018/0325412 A1 Nov. 15, 2018
US 2019/0150780 A2 May 23, 2019

Related U.S. Application Data

(63) Continuation of application No. PCT/US2017/049191, filed on Aug. 29, 2017.
(Continued)

(51) Int. Cl.
*A61B 5/00* (2006.01)
*A61B 5/055* (2006.01)
(Continued)

(52) U.S. Cl.
CPC ............ *A61B 5/055* (2013.01); *A61B 5/0555* (2013.01); *A61B 5/1071* (2013.01);
(Continued)

(58) Field of Classification Search
CPC ....... A61B 5/055; A61B 5/6835; A61B 90/11; A61B 6/04; A61B 5/1071; A61B 5/1127;
(Continued)

(56) References Cited

U.S. PATENT DOCUMENTS

RE42,856 E    10/2011  Karmarkar et al.
8,055,351 B2  11/2011  Atalar et al.
(Continued)

OTHER PUBLICATIONS

Larson et al. (2012) "An Optimized System for Interventional MRI Guided Stereotactic Surgery: Preliminary Evaluation of Targeting Accuracy" Neurosurgery 70(Operative): ons95-ons103, pp. 1-18.
(Continued)

*Primary Examiner* — Joel Lamprecht
(74) *Attorney, Agent, or Firm* — Edward J. Baba; Bozicevic, Field & Francis LLP

(57) ABSTRACT

The present disclosure provides methods for targeting a biomedical system. Aspects of the subject methods include determining the trajectory of a targeting device using magnetic resonance imaging (MRI) of a MRI-visible style of a trajectory guide that is compatible with the targeting device. Targeted biomedical systems may be utilized for a variety of purposes including targeted delivery of a therapeutic, holding a therapeutic device, positioning of a therapeutic device and other uses. Also provided are devices and systems that can be used in practicing the described methods including but not limited to trajectory guides and adjustable targeting systems, as well as non-transitory computer readable medium storing instructions that, when executed by a computing device, cause a computing device to perform steps of the described methods.

25 Claims, 10 Drawing Sheets

Related U.S. Application Data

(60) Provisional application No. 62/381,423, filed on Aug. 30, 2016.

(51) Int. Cl.
    *A61B 6/03*     (2006.01)
    *A61B 6/04*     (2006.01)
    *A61B 5/107*     (2006.01)
    *A61B 5/11*     (2006.01)
    *A61B 90/11*     (2016.01)
    *A61B 34/10*     (2016.01)
    *A61B 17/00*     (2006.01)

(52) U.S. Cl.
CPC .......... *A61B 5/1072* (2013.01); *A61B 5/1127* (2013.01); *A61B 5/6835* (2013.01); *A61B 6/03* (2013.01); *A61B 6/04* (2013.01); *A61B 90/11* (2016.02); *A61B 34/10* (2016.02); *A61B 2017/00911* (2013.01); *A61B 2034/107* (2016.02); *A61B 2505/05* (2013.01); *A61B 2560/0475* (2013.01); *A61B 2576/026* (2013.01)

(58) Field of Classification Search
CPC ....... A61B 6/03; A61B 5/1072; A61B 5/0555; A61B 2017/00911; A61B 2034/107; A61B 34/10; A61B 2560/0475; A61B 2576/026; A61B 2505/05

See application file for complete search history.

(56) References Cited

U.S. PATENT DOCUMENTS

| | | | |
|---|---|---|---|
| 8,099,150 B2 | 1/2012 | Piferi et al. | |
| 8,157,828 B2 | 4/2012 | Piferi | |
| 8,175,677 B2 | 5/2012 | Sayler et al. | |
| 8,195,272 B2 | 6/2012 | Piferi et al. | |
| 8,208,993 B2 | 6/2012 | Piferi et al. | |
| 8,315,689 B2 | 11/2012 | Jenkins et al. | |
| 8,320,990 B2 | 11/2012 | Vij | |
| 8,340,743 B2 | 12/2012 | Jenkins et al. | |
| 8,369,930 B2 | 2/2013 | Jenkins et al. | |
| 8,374,677 B2 | 2/2013 | Piferi et al. | |
| 8,380,277 B2 | 2/2013 | Atalar et al. | |
| 8,396,532 B2 | 3/2013 | Jenkins et al. | |
| 8,433,421 B2 | 4/2013 | Atalar et al. | |
| 8,460,328 B2 | 6/2013 | Piferi | |
| 8,548,569 B2 | 10/2013 | Piferi et al. | |
| RE44,736 E | 1/2014 | Karmarkar et al. | |
| 8,644,906 B2 | 2/2014 | Piferi et al. | |
| 8,649,842 B2 | 2/2014 | Atalar et al. | |
| 8,688,226 B2 | 4/2014 | Atalar et al. | |
| 8,768,433 B2 | 7/2014 | Jenkins et al. | |
| 8,825,133 B2 | 9/2014 | Jenkins et al. | |
| 8,886,288 B2 | 11/2014 | Jenkins et al. | |
| 8,909,320 B2 | 12/2014 | Jenkins et al. | |
| 9,031,636 B2 | 5/2015 | Piferi | |
| 9,042,958 B2 | 5/2015 | Karmarkar et al. | |
| 9,055,884 B2 | 6/2015 | Piferi et al. | |
| 9,078,588 B2 | 7/2015 | Ghidoli et al. | |
| 9,097,756 B2 | 8/2015 | Piferi | |
| 9,179,857 B2 | 11/2015 | Lee et al. | |
| 9,192,393 B2 | 11/2015 | Piferi et al. | |
| 9,192,446 B2 | 11/2015 | Piferi et al. | |
| 9,242,090 B2 | 1/2016 | Atalar et al. | |
| 9,248,270 B2 | 2/2016 | Karmarkar et al. | |
| 9,259,290 B2 | 2/2016 | Jenkins et al. | |
| 9,314,305 B2 | 4/2016 | Jenkins et al. | |
| 9,345,875 B2 | 5/2016 | Appenrodt et al. | |
| 2004/0167391 A1* | 8/2004 | Solar | A61B 90/39 600/411 |
| 2009/0112084 A1 | 4/2009 | Piferi et al. | |
| 2009/0118610 A1* | 5/2009 | Karmarkar | A61B 5/0476 600/420 |
| 2011/0224478 A1* | 9/2011 | Hannoun-Levi | A61N 5/1016 600/6 |
| 2012/0078087 A1 | 3/2012 | Curry | |
| 2015/0230871 A1 | 8/2015 | Sayler et al. | |

OTHER PUBLICATIONS

Potts et al. (2013) "Devices for cell transplantation into the central nervous system: Design considerations and emerging technologies" Surg Neurol Int 4(1): S22-S30.

\* cited by examiner

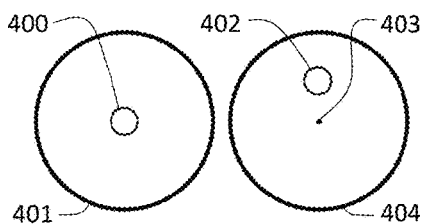
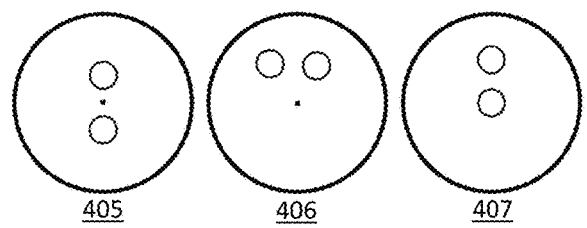
FIG. 4A
FIG. 4B
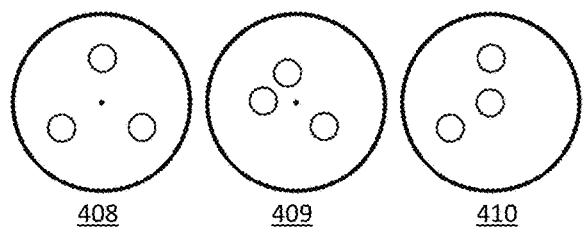
FIG. 4C
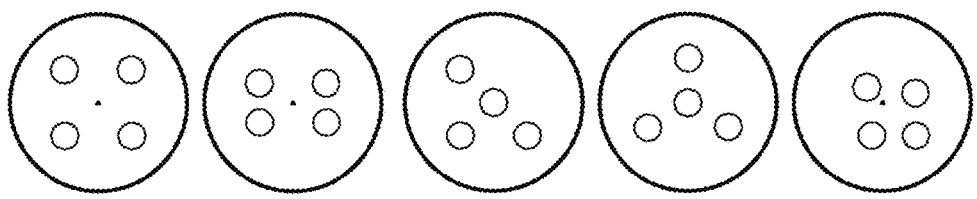
FIG. 4D
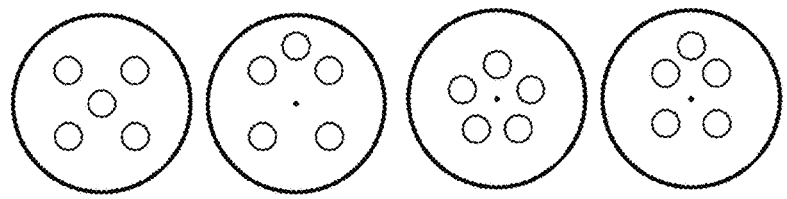
FIG. 4E
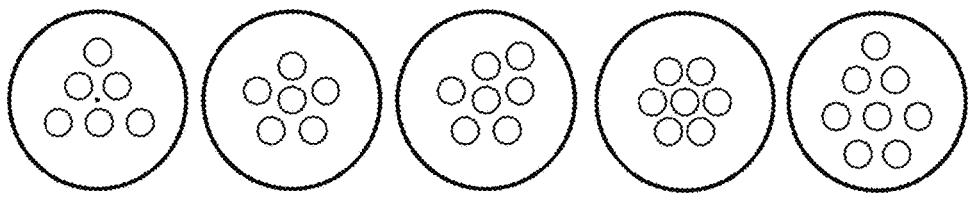
FIG. 4F

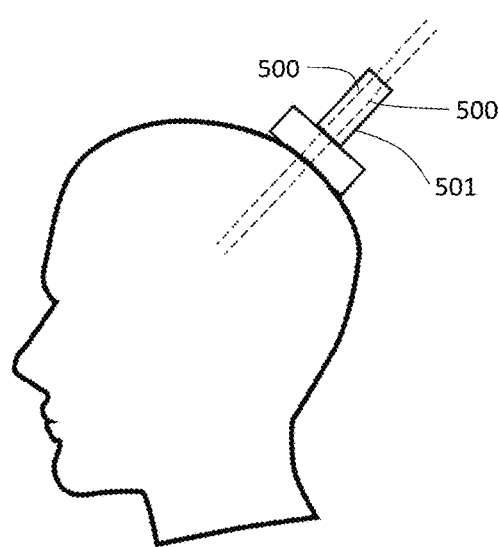
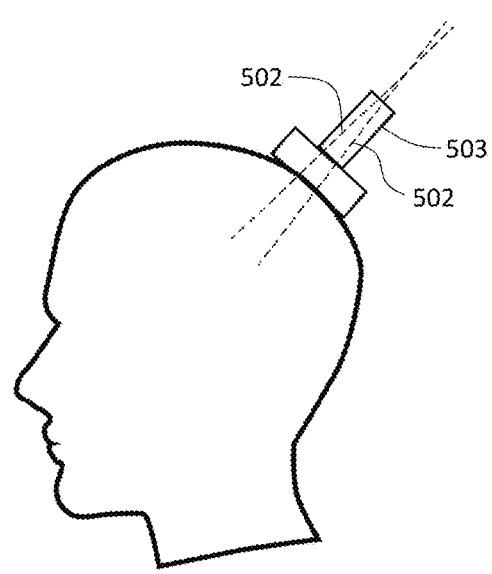
FIG. 5A				FIG. 5B
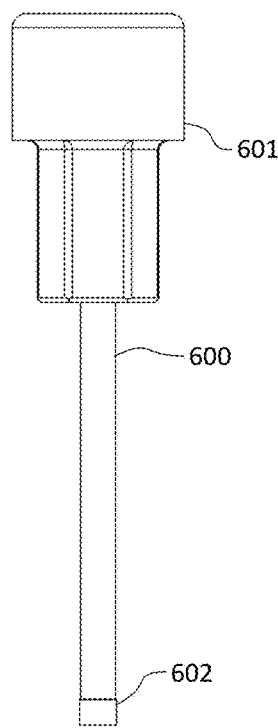
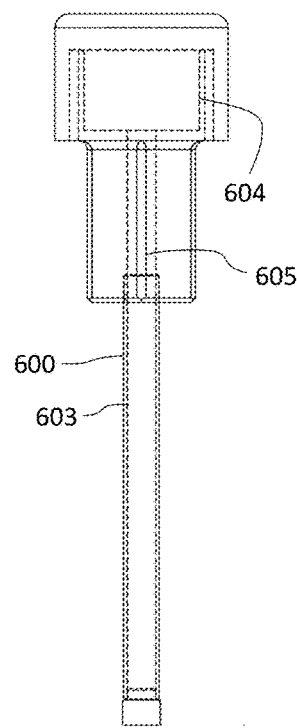
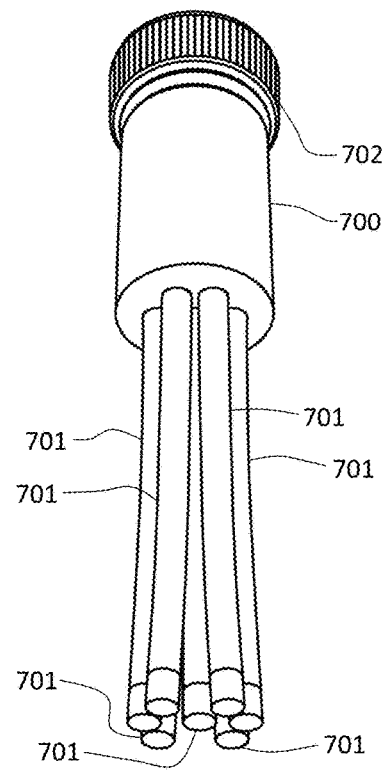
FIG. 6A		FIG. 6B		FIG. 7A

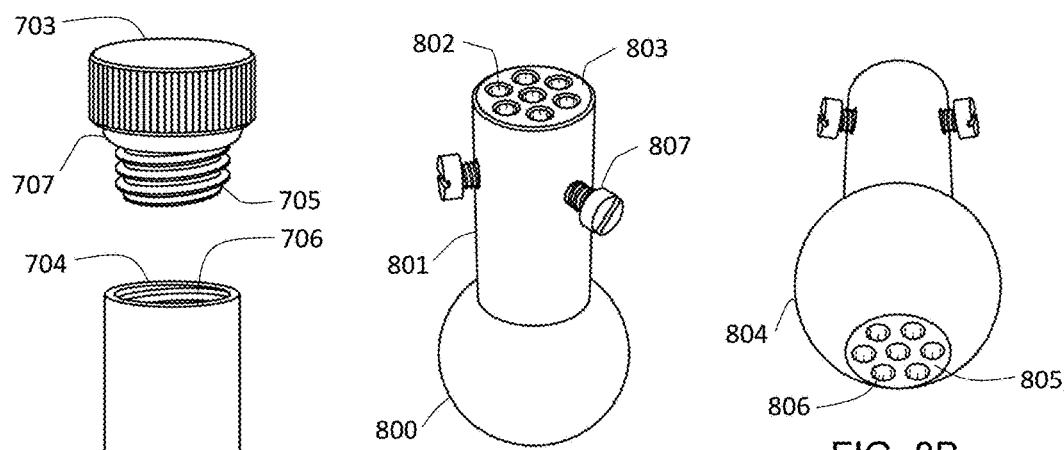
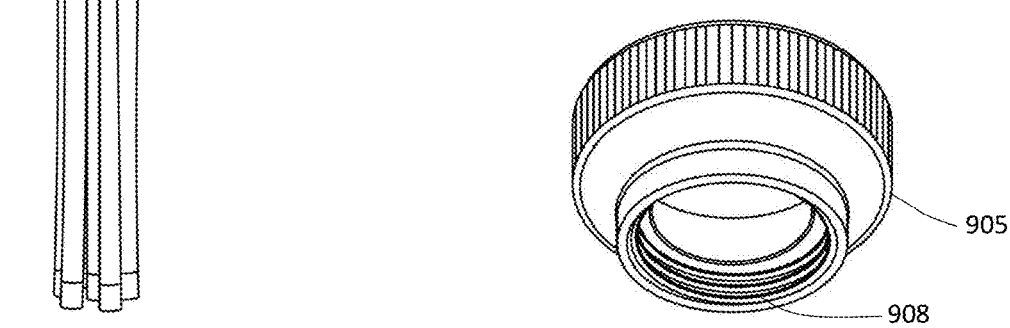
FIG. 7B
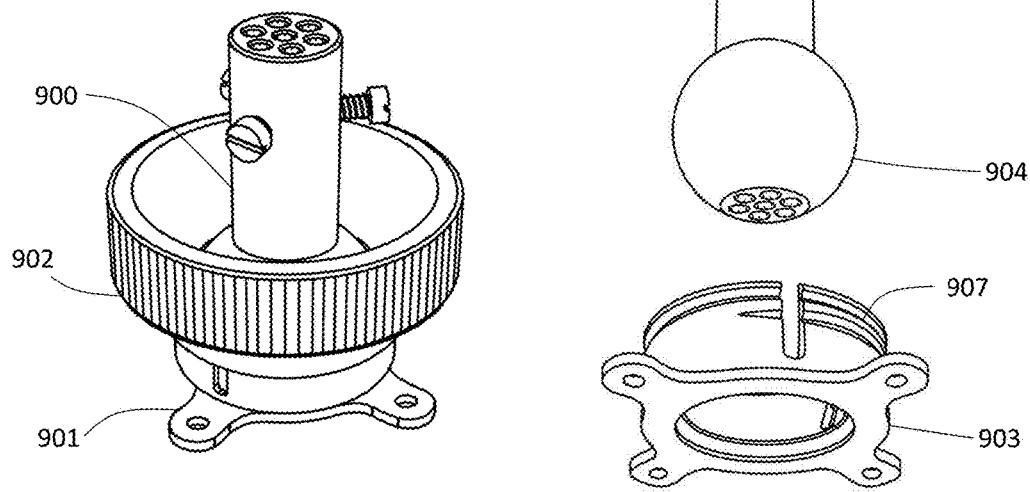
FIG. 9A        FIG. 9B

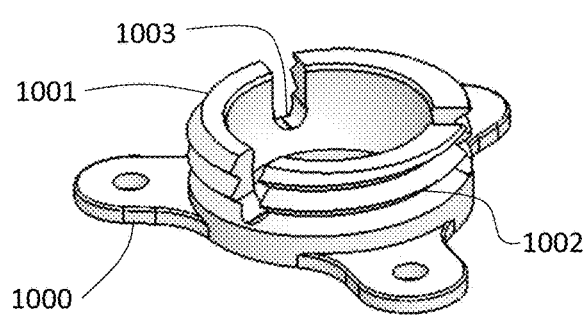
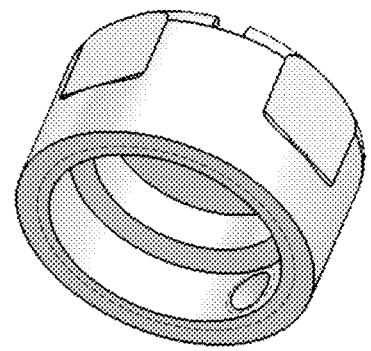
FIG. 10  FIG. 11
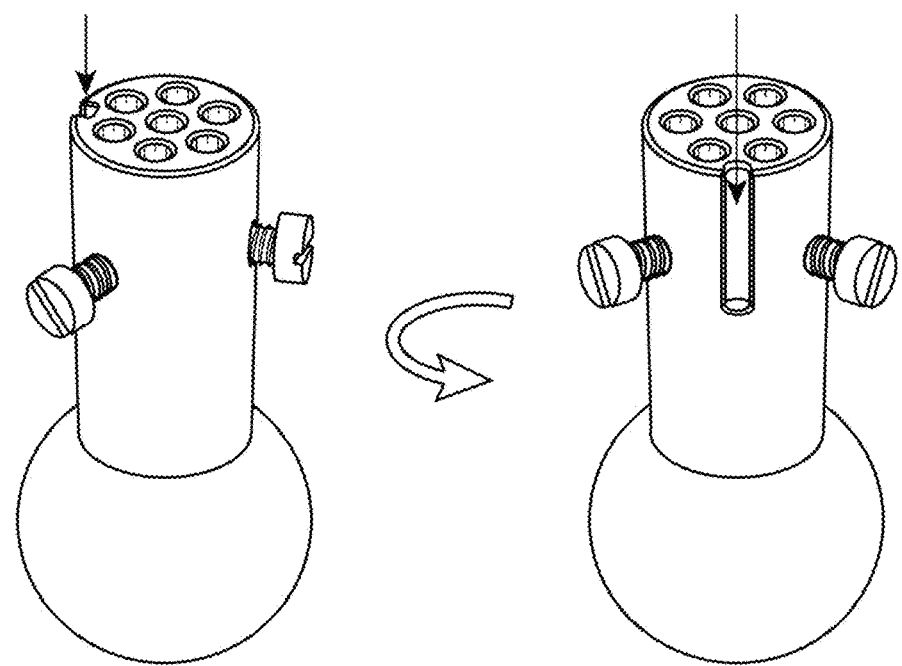
FIG. 12

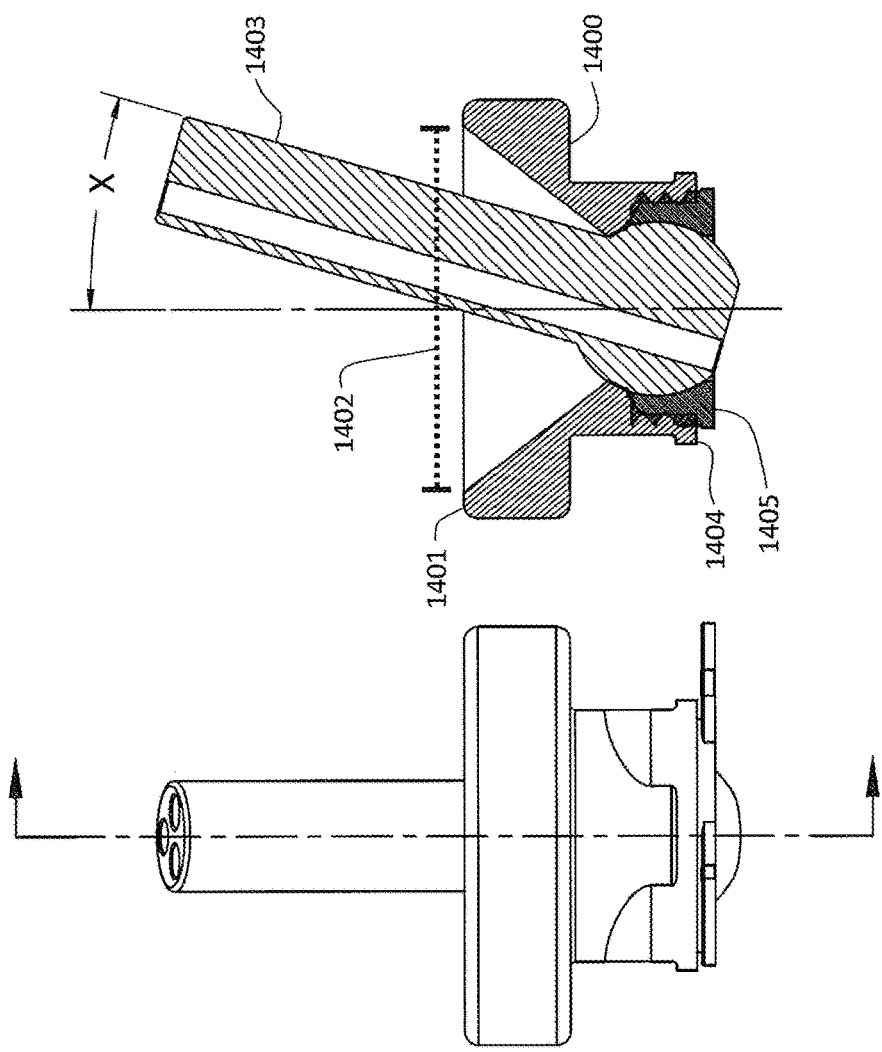
FIG. 14C
FIG. 14B
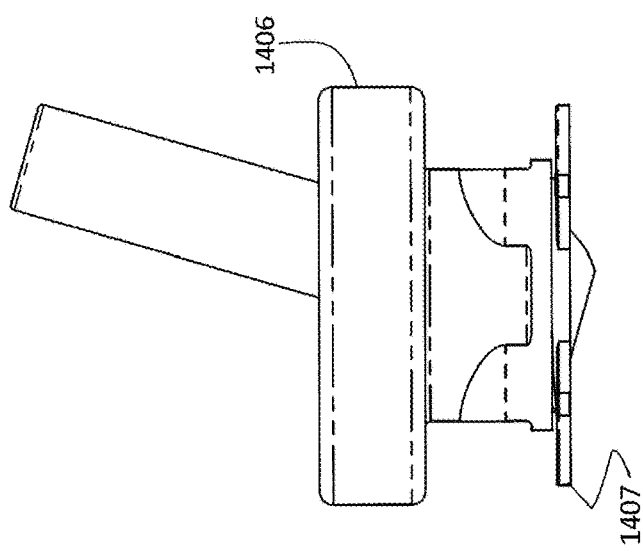
FIG. 14A

METHODS FOR BIOMEDICAL TARGETING AND DELIVERY AND DEVICES AND SYSTEMS FOR PRACTICING THE SAME

CROSS-REFERENCE TO RELATED APPLICATIONS

This application is a continuation of PCT/US2017/049191, filed Aug. 29, 2017, which claims the benefit of U.S. Provisional Patent Application No. 62/381,423, filed Aug. 30, 2016, which application is incorporated herein by reference in its entirety.

STATEMENT REGARDING FEDERALLY SPONSORED RESEARCH

This invention was made with government support under Grant No. P01 CA118816 awarded by the National Institutes of Health. The government has certain rights in the invention.

BACKGROUND

Many biomedical applications using advanced drugs and therapeutic techniques still require that the drug be delivered or the therapy be applied to a precise location within the subject. Thus, proper therapeutic targeting remains an important aspect of many therapeutic procedures regardless of treatment modality.

Exemplary areas of biomedicine where precise targeting is advantageous include neurological medicine and neurosurgery. For example, treatment of central nervous system disorders can be challenging due to the protected compartmentalization of the brain and spinal cord by the blood-brain barrier. In many circumstances, microinjections into the brain parenchyma are important procedures to deliver drugs, viral vectors or cell transplants. Many brain diseases remain under treated because of a lack of sufficiently precise and easy to use brain targeting systems that can efficiently assist a healthcare provider in delivering a therapeutic agent locally to the disease site in the brain while minimizing residual damage to surrounding brain structures. Besides agent delivery, neuroablation within the brain and intracranial surgery facilitates the treatment of debilitating neurological disorders characterized by malfunctioning neurons such as epilepsy and malignant tissue such as brain tumors. Like precise agent delivery, these techniques require a high level of accuracy to be effective.

The benefit of precise targeting of therapeutic interventions is not limited to neurological disorders and may include essentially any treatment paradigm where the location of the affected tissues or the origin of disease producing cells is known.

SUMMARY

The present disclosure provides methods for targeting a biomedical system. Aspects of the subject methods include determining the trajectory of a targeting device using magnetic resonance imaging (MRI) of a MRI-visible style of a trajectory guide that is compatible with the targeting device. Targeted biomedical systems may be utilized for a variety of purposes including targeted delivery of a therapeutic, holding a therapeutic device, positioning of a therapeutic device and other uses. Also provided are devices and systems that can be used in practicing the described methods including but not limited to trajectory guides and adjustable targeting systems, as well as non-transitory computer readable medium storing instructions that, when executed by a computing device, cause a computing device to perform steps of the described methods.

Aspects of the present disclosure include a method of magnetic resonance imaging (MRI)-assisted targeting of a desired area of a subject, the method comprising: positioning an adjustable turret comprising a channel on a tissue surface of a subject; inserting a MRI-visible style of a trajectory guide within the channel of the adjustable turret; visualizing the MRI-visible style using an MRI imager; determining the trajectory of the channel based on the visualizing; and adjusting the adjustable turret based on the determined trajectory of the channel to target the desired area of the subject.

In some embodiments the adjustable turret is positioned ex vivo. In some embodiments, the method further comprises affixing a base to the tissue surface of the subject and mounting the adjustable turret to the base. In some embodiments, the base is positioned ex vivo. In some embodiments, the base comprises a flange and the affixing comprises mounting a fastener through the flange to affix the base to the tissue surface of the subject. In some embodiments, the method further comprises locking the adjustable turret in place following the adjusting. In some embodiments, the locking comprises tightening a locking collar to compress the adjustable turret between the locking collar and the base. In some embodiments, the locking comprises tightening a locking collar to compress the adjustable turret between a plurality of annular walls of the base. In some embodiments, the channel is not coaxial with the turret. In some embodiments, the adjusting comprises a roll adjustment relative to the long axis of the adjustable turret. In some embodiments, the adjusting comprises an angle adjustment relative to the long axis of the adjustable turret. In some embodiments, the adjustable turret comprises a plurality of channels. In some embodiments, the trajectory guide comprises a plurality of MRI-visible styles. In some embodiments, the trajectory guide has the same number of styles as the adjustable turret has channels.

Aspects of the present disclosure include a method of magnetic resonance imaging (MRI)-assisted delivery of an agent or an electrical current to a desired area of a subject, the method comprising: targeting the desired area of the subject according to any of the methods described above; removing the MRI-visible style from the channel following the adjusting; and delivering the agent or the electrical current through the channel to the desired area of the subject.

In some embodiments, the method comprises MRI-assisted delivery of an agent and the delivering comprises inserting a delivery device containing the agent into the channel. In some embodiments, the delivery device comprises a needle or cannula. In some embodiments, the agent is a gene therapy vector. In some embodiments, the delivery device comprises a depth stop positioned at a point along the length of the delivery device to prevent inserting the delivery device into the channel past said point. In some embodiments, the method comprises MRI-assisted delivery of an electrical current and the delivering comprises inserting an electrode into the channel. In some embodiments, the electrode comprises a depth stop positioned at a point along the length of the electrode to prevent inserting the electrode into the channel past said point.

Aspects of the present disclosure include a method of magnetic resonance imaging (MRI)-assisted delivery of an agent or an electrical current to a desired area of a subject, the method comprising: positioning an adjustable turret comprising a plurality of channels on a tissue surface of a subject; inserting each of a plurality of MRI-visible styles of a trajectory guide within each of the plurality of channels of the adjustable turret;

visualizing the plurality of MRI-visible styles using an MRI imager; determining the trajectory of two or more channels of the plurality of channels based on the visualizing; identifying a channel of the two or more channels with the trajectory closest to the desired area of the subject; and delivering the agent or the electrical current through the channel with the trajectory closest to the desired area of the subject.

In some embodiments, the method further comprises adjusting the adjustable turret based on the determined trajectory of the identified channel to target said channel to the desired area of the subject.

Aspects of the present disclosure include a trajectory guide for magnetic resonance imaging (MRI)-assisted targeting of a desired area of a subject, comprising: a solid support comprising a flat surface; a MRI-visible style comprising a lumen comprising a contrast agent, wherein the MRI-visible style is affixed at one end to the flat surface and dimensioned for insertion into a channel of an adjustable turret affixed to a tissue surface of a subject thereby allowing targeting of the channel by visualizing the trajectory of the inserted MRI-visible style using an MRI imager.

In some embodiments, the trajectory guide comprises a plurality of MRI-visible styles. In some embodiments, the plurality of MRI-visible styles comprises two or more styles that are affixed symmetrically to the flat surface with respect to the geometric center of the flat surface. In some embodiments, the plurality of MRI-visible styles comprises at least one style that is affixed asymmetrically to the flat surface with respect to one or more styles of the plurality. In some embodiments, at least one MRI-visible style is affixed perpendicular to the flat surface. In some embodiments, at least one MRI-visible style is affixed at a flared angle to the flat surface. In some embodiments, the solid support comprises an opening, opposite the flat surface, adjoining a void within the solid support that is contiguous with the lumen of the MRI-visible style thereby allowing access to the void and the lumen. In some embodiments, the trajectory guide further comprises a cap for closing the opening. In some embodiments, the cap and the opening comprise compatible threading. In some embodiments, the contrast agent comprises gadolinium.

Aspects of the present disclosure include, an adjustable targeting system, the system comprising: an adjustable turret comprising a distal end, a spherical end and one or more channels running from the distal end to the spherical end; a base, comprising: a plurality of annular walls forming a socket dimensioned to receive the spherical end, threading on an external surface of the annular walls; a plurality of slots positioned between the plurality of annular walls; and a flange orthogonal to at least one of the annular walls for affixing the base to a tissue surface of a subject; and a locking collar comprising threading on an internal surface compatible with the threading on the external surface of the base, wherein turning the locking collar a first direction compresses the spherical end to lock the adjustable turret in a desired trajectory and turning the locking collar a second direction decompresses the spherical end to allow for retargeting of the trajectory of the adjustable turret.

In some embodiments, turning the locking collar the first direction compresses the spherical end between the base and the locking collar to lock the adjustable turret in a desired trajectory. In some embodiments, turning the locking collar the first direction compresses the spherical end between the plurality of annular walls of the socket to lock the adjustable turret in a desired trajectory. In some embodiments, the adjustable targeting system is configured such that when affixed to the tissue surface of the subject the base and the locking collar are ex vivo. In some embodiments, the adjustable targeting system is configured such that when affixed to the tissue surface of the subject the adjustable turret is ex vivo. In some embodiments, the spherical end comprises a flat portion opposite the distal end that comprises openings to the one or more channels. In some embodiments, the spherical end and the flat portion are dimensioned such that, when inserted into the socket, the flat portion is flush with the bottom surface of the base. In some embodiments, the locking collar comprises a knurled external surface to provide grip. In some embodiments, the base comprises a plurality of flanges orthogonal to at least one of the annular walls. In some embodiments, the system further comprises a trajectory guide according to any of those described above. In some embodiments, the system further comprises an MRI imager positioned to image a MRI-visible style of the trajectory guide when the MRI-visible style is inserted into a channel of the adjustable turret.

Aspects of the present disclosure include an adjustable targeted delivery system, the system comprising: an adjustable targeting system according to any of those described above; and a delivery device or electrode dimensioned for insertion into the one or more channels of the adjustable turret.

In some embodiments, the delivery device or electrode comprises a depth stop positioned at a point along the length of the delivery device or electrode to prevent inserting the delivery device into the one or more channels past said point.

Aspects of the present disclosure include, a non-transitory computer readable medium storing instructions that, when executed by a computing device, cause the computing device to perform the steps of: receiving a magnetic resonance image (MRI) of a trajectory guide MRI-visible style inserted within a channel of an adjustable turret; determining the trajectory of the channel based on the received MRI; comparing the determined trajectory to a desired user input trajectory; calculating a recommended adjustment of the adjustable turret necessary to align the determined trajectory with the desired user input trajectory based on the comparing; and displaying the recommended adjustment.

Aspects of the present disclosure include an automated adjustable targeting system, the system comprising: an adjustable targeting system according to those described above; an actuator connected to the adjustable turret and controlled by a processor programmed with instructions that, when executed by the processor, cause the processor to: determine the trajectory of a channel of the adjustable turret based on a received magnetic resonance image (MRI) of a trajectory guide MRI-visible style inserted within the channel; compare the determined trajectory to a desired user input trajectory; calculate an adjustment of the adjustable turret necessary to align the determined trajectory with the desired user input trajectory based on the comparing; and trigger the actuator to execute the adjustment thereby aligning the determined trajectory with the desired user input trajectory.

BRIEF DESCRIPTION OF THE FIGURES

FIGS. 4A-4F provide exemplary arrangements of channels within a turret or styles of a trajectory guide as described herein.

FIGS. 5A-5B depict targeting device turrets having parallel and nonparallel channels.

FIGS. 6A-6B depict a targeting guide and a cutaway thereof according to an embodiment described herein.

FIGS. 7A-7B depict a targeting guide having a plurality of MRI-visible styles according to an embodiment described herein.

FIGS. 8A-8B depict adjustable turrets of a targeting device as described herein.

FIGS. 9A-9B depict an assembled and unassembled multi-component targeting device as described herein.

FIG. 10 depicts a base of a multi-component targeting device as described herein.

FIG. 11 depicts a cap configured for attachment to a base of a multi-component targeting device as described herein.

FIG. 12 depicts an adjustable turret of a targeting device having an asymmetry groove.

FIGS. 14A-14C depict an assembled ex vivo targeting system according to an embodiment described herein.

DEFINITIONS

Figure 1:
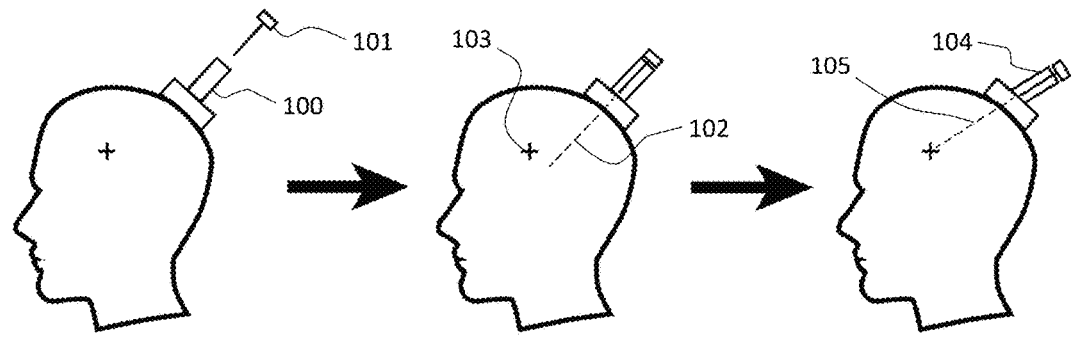
FIG. 1 depicts a method of targeting a device to a desired region according to an embodiment described herein.

As used herein, "treatment" or "treating" refers to inhibiting the progression of a disease or disorder, or delaying the onset of a disease or disorder, whether physically, e.g., stabilization of a discernible symptom, physiologically, e.g., stabilization of a physical parameter, or both. As used herein, the terms "treatment," "treating," and the like, refer to obtaining a desired pharmacologic and/or physiologic effect. The effect may be prophylactic in terms of completely or partially preventing a disease or condition, or a symptom thereof and/or may be therapeutic in terms of a partial or complete cure for a disease or disorder and/or adverse effect attributable to the disease or disorder. "Treatment," as used herein, covers any treatment of a disease or disorder in a mammal, such as a human, and includes: decreasing the risk of death due to the disease; preventing the disease of disorder from occurring in a subject which may be predisposed to the disease but has not yet been diagnosed as having it; inhibiting the disease or disorder, i.e., arresting its development (e.g., reducing the rate of disease progression); and relieving the disease, i.e., causing regression of the disease. Therapeutic benefits of the present invention include, but are not necessarily limited to, reduction of risk of onset or severity of disease or conditions associated with neurological conditions.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute.

The term "inputting", as used herein, is used to refer to any way of entering information into a computer, such as, e.g., through the use of a user interface. For example, in certain cases, inputting can involve selecting a target or trajectory that is already present or identified on a computer system. In other cases, inputting can involve target or trajectory to a computer system, e.g., by defining a target or trajectory on an image within the computer system with or without first generating the image on a device capable of interfacing with a computer. As such, inputting can be done using a user interface, using a device configured to send information to the computer system, such as an image capture device, or any combination thereof.

By "data processing unit", as used herein, is meant any hardware and/or software combination that will perform the functions required of it. For example, any data processing unit herein may be a programmable digital microprocessor such as available in the form of an electronic controller, mainframe, server or personal computer (desktop or portable). Where the data processing unit is programmable, suitable programming can be communicated from a remote location to the data processing unit, or previously saved in a computer program product (such as a portable or fixed computer readable storage medium, whether magnetic, optical or solid state device based). Data processing units may, in some instances, be specialized for particular purpose, such as, e.g., an image processing unit specialized to receive and process image data.

As used herein, the term "executing" is used to refer to an action that a user takes to initiate a program.

DETAILED DESCRIPTION

The present disclosure provides methods for targeting a biomedical system. Aspects of the subject methods include determining the trajectory of a targeting device using magnetic resonance imaging (MRI) of a MRI-visible style of a trajectory guide that is compatible with the targeting device. Targeted biomedical systems may be utilized for a variety of purposes including targeted delivery of a therapeutic, holding a therapeutic device, positioning of a therapeutic device and other uses. Also provided are devices and systems that can be used in practicing the described methods including but not limited to trajectory guides and adjustable targeting systems, as well as non-transitory computer readable medium storing instructions that, when executed by a computing device, cause a computing device to perform steps of the described methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

The instant disclosure provides methods for targeting a biomedical system. By "biomedical system" is meant any device or system of components used in medical or therapeutic applications including but not limited to treatment of a subject, diagnosis of a condition of a subject, biomedical research performed on a subject, and the like. Aspects of the subject methods generally, but not exclusively, include positioning a targeting device on the surface of a subject and establishing, aligning and/or adjusting the trajectory of the targeting device for one or more downstream applications that rely on the trajectory of the targeting device for proper placement of a medical device on or within the subject. In some instances, aspects of the subject methods may also include utilizing the herein described devices, or components thereof, as a holder for therapeutic administration devices including but not limited to e.g., drug delivery devices, viral vector delivery devices, nanoparticle delivery devices, cell administration delivery devices, cell delivery devices, and the like. The actual configuration of a targeting device of the subject disclosure will vary.

In some instances, a targeting device of the subject disclosure may include an adjustable turret having one or more channels, the trajectory of which is relied upon for proper positioning of a medical device inserted into one or more of the channels. According to some embodiments, the targeting device may be attached to the surface of a subject and adjusting the adjustable turret allows for adjusting the trajectory of the one or more channels of the turret to better target a desired area of the subject or to avoid an obstacle within the subject.

A targeting device may be initially positioned on a tissue surface of a subject. The initial position of the targeting device on the subject will vary depending on a number of factors including the position of one or more desired target areas of the subject, the position of one or more obstacles within the subject, and the like. In some instances, the tissue surface of the subject to which the targeting device is attached, establishing the initial position, is chosen because it is the tissue surface closest to a desired area on or into which a medical device is to be positioned. In some instances, the initial position is chosen because it is an accessible tissue surface, which may or may not be the closest accessible tissue surface to a desired area on or into which a medical device is to be positioned. In some instances, the initial positioning of the targeting device takes into account the underlying position of obstacles or likely underlying position of likely obstacles. For example, in some instances, the tissue surface closest to a desired area of a subject may not be used because doing so may require that the medical device be inserted through an obstacle or increase the chances that the medical device be inserted through an obstacle. In some instances, the initial positioning may not take into account the position of obstacles or the likely position of obstacles and the targeting device may be positioned and any obstacles may be subsequently avoided during targeting, e.g., as described further herein.

In some instances, the tissue surface upon which the targeting device is initially affixed may be first prepared for affixing the targeting device. Various methods of preparing the surface may be employed including but not limited to e.g., shaving or otherwise removing hair from the surface, cleaning and/or sterilizing the surface (e.g., by applying an alcohol, an alcohol-based cleaner, an iodine based-cleaner (e.g., povidone-iodine) solution, chlorhexidine gluconate, or the like), removing one or more layers of skin from the surface, covering the surface with a protective cover (e.g., a plastic adhesive drape), etc. In some instances, the surface may be prepared according to the current Association of Surgical Technologists (AST) Standards of Practice for Skin Prep of the Surgical Patient (e.g., as available online at www(dot)ast(dot)org). In some instances, the surface of the subject may not be prepared or may be minimally prepared prior to placing the targeting device including e.g., when used in an emergency application or field setting.

In some instances, the targeting device includes a base, either removable or non-removable, that can be used to affix the targeting device to a tissue surface of a subject. Various methods may be employed for attaching the base to the tissue surface of the subject. For example, in some instances, the base may be attached to the subject through the use of one or more adhesives including but not limited to surgical adhesives, dental acrylic, surgical/skin tape, etc. However, the use of adhesives is not necessarily required and, in some instances, the base is attached without the use of adhesive. In some instances, whether or not adhesives are used, the base may be attached to the subject through one or more fasteners including but not limited to e.g., sutures, buttons, staples, clips, screws, etc. As described in more detail below, in some instances, the base of the targeting device may include one or more features to facilitate attachment of the base to the subject including but not limited to e.g., a flange, a notch, an adhesion surface, etc. In some instances, a fastener may be placed through such a feature including e.g., where a screw is placed through a flange to attach the base to the subject, e.g., by screwing the base to a solid tissue of the subject including e.g., cartilage, bone, etc.

The base of the device may be attached directly to the tissue surface of the subject or may be attached indirectly including e.g., through the use of one or more intermediate structures including e.g., an attachment plate, an attachment frame, etc. Intermediate structures may be used in various situations including e.g., where the tissue to which the base would be otherwise attached is insufficient (e.g., of insufficient size, of insufficient density or rigidity for a desired method of attachment, etc.) for attachment of the base. For example, an intermediate structure (e.g., a frame or a plate) could be used when the base is to be positioned over a soft tissue of the subject, e.g., the eye of a subject, for device insertion into or near the soft tissue, e.g., the eye. However, such situations do not necessarily require an intermediate structure and in some instances e.g., the base could be attached directly to a small or less dense tissue of the subject including e.g., the eye.

In some instances, the targeting device may be attached to the subject such that all or nearly all components of the device remain outside the subject. In some instances throughout the instant disclosure such attachment may be referred to as substantially ex vivo, ex vivo and/or completely ex vivo. For example, the device may be attached such that the base is flush or nearly flush with the surface of the subject but remains substantially ex vivo or completely ex vivo. In some instances, the device may be attached such that the turret is flush or nearly flush with the surface of the subject but remains ex vivo. Components of certain devices that are intentionally inserted into the subject, including e.g., a delivery device, an electrode, a camera, attachment fasteners, etc., are generally not considered when a device is described as substantially ex vivo and/or completely ex vivo. As such, in some instances, a device may be simply described as ex vivo without addressing the inserted component or may be specifically described as ex vivo excluding the intentionally inserted component(s).

Following the attachment of the targeting device to the subject an adjustable turret of the device, and the channel(s) thereof, will generally have or be placed in an initial position or orientation. For example, in some instances, the turret may be arbitrarily positioned initially including e.g., arbitrarily positioned perpendicular to the attachment surface. In some instances, the turret may be initially positioned to approximate a desired trajectory. The initial position of the turret generally refers to the position of the turret following attachment to the subject but prior to any imaging-based adjustments of the turret.

Aspects of the instant methods include using a trajectory guide to determine the trajectory of one or more channels of an adjustable turret. As used herein the term "trajectory guide" generally refers to a device, described in more detail below, having one or more MRI-visible styles that can be inserted into one or more channels of an adjustable turret and imaged using an MRI to allow for a determination of the trajectory of the channel to be made. Thus, MRI visualization of the styles of a trajectory guide allow for simultaneous visualization of both the trajectory of the channel(s) and the target area and/or any obstacles within or near the trajectory.

Referring now to the example presented in FIG. 1, a targeting device of the instant disclosure is attached to the head of a subject. Then, to determine the trajectory of a channel within an adjustable turret (100) a style of a trajectory guide (101) is inserted into the channel and the system is subsequently MRI imaged. Following the imaging, the initial trajectory (102) of the channel may be determined based on the MRI-visible style and the relative positions of the initial trajectory and a targeted area of the subject's brain (103) may be determined. Once any difference between the position of the trajectory and the position of the targeted area of the brain are known, an adjustment may be made to bring the trajectory and the targeted position of the brain into alignment. For example, an angle adjustment of the adjustable turret (104) may be made to result in an adjusted trajectory (105) that aligns the adjusted trajectory or more closely aligns the adjusted trajectory with the target area.

Figure 2:
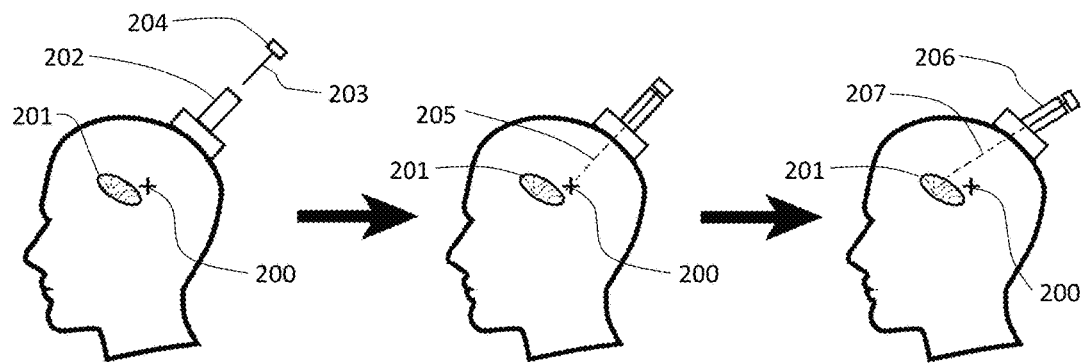
FIG. 2 depicts a method of targeting a device to a desired region while avoiding an obstacle according to an embodiment described herein.

Adjustments of a targeting device are not limited to those used to improve the targeting of a desired area of subject. For example, as depicted in FIG. 2, in some instances, targeting adjustments may be made to avoid an obstacle (200). In the embodiment depicted, a desired area of a subject's brain (201) is targeted using a targeting device having an adjustable turret (202). The MRI-visible style (203) of a targeting guide (204) is inserted into the adjustable turret (202) and the initial trajectory is determined (205). In the embodiment depicted, although the determined trajectory (205) is sufficient to target the desired area of the subject's brain (201) it is discovered that an obstacle (200) is in the path of the trajectory. Accordingly, an angle adjustment of the adjustable turret is made (206) that results in a desired trajectory (207) that sufficiently targets the desired area of a subject's brain (201) while avoiding the obstacle (200). In some instances, the necessary adjustment to achieve the desired trajectory is calculated prior to making the adjustment, e.g., so that a minimal number of adjustments must be made to achieve the desired trajectory, in what may be referred to as a "calculated" or "predetermined" approach. In some instances, the adjustment is made without calculating what adjustment is necessary and the adjusted trajectory is analyzed to determine if it achieves a desired trajectory (e.g., targets the desired area, avoids one or more obstacles, etc.) in what is commonly referred to as a "guess-and-check" approach.

Depicted in FIG. 1 and FIG. 2 are angle adjustments where an angle adjustment can be defined as modifying the angle of the adjustable turret relative to the long axis of the adjustable turret about a pivot point defined by the portion of the turret that rests within the base of the trajectory device. Accordingly, an angle adjustment may be measured using any convenient means and may be represented as the change in degrees between a starting trajectory and a modified trajectory. Useful angle adjustments will vary and will depend on a number of factors including e.g., the initial trajectory, the specific configuration of the targeting device, the size of the area to be targeted, etc. In some instances, an angle adjustment may range from 0.1° or less to 60° of more where the maximum angle adjustment may be limited by the configuration of the targeting device including components or parameters of the targeting device that physically prevent greater adjustment including but not limited to e.g., the size of the rounded end of the adjustable turret, the diameter of the turret, the size and shape of a locking ring, etc. In some instances, an angle adjustment may range from 0.1° to 60° including but not limited to e.g., 0.1° to 55°, 0.1° to 50°, 0.1° to 45°, 0.1° to 40°, 0.1° to 35°, 0.1° to 30° and the like.

As will be readily understood, adjustments of the adjustable turret are not limited to angle adjustments and may also include, e.g., roll adjustments. As used herein, the term "roll adjustment" generally refers to rotating the adjustable turret about its long axis. While roll adjustments may not change the trajectory of a channel that is coaxial with the adjustable turret, roll adjustments will modify the trajectory of channels that are not coaxial with the turret. In making roll adjustments the adjustable turret may be rotated essentially any amount up to 360° including but not limited to e.g., 1°, 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175°, 180°, 185°, 190°, 195°, 200°, 205°, 210°, 215°, 220°, 225°, 230°, 235°, 240°, 245°, 250°, 255°, 260°, 265°, 270°, 275°, 280°, 285°, 290°, 295°, 300°, 305°, 310°, 315°, 320°, 325°, 330°, 335°, 340°, 345°, 350°, 355°, and the like.

Determinations of the trajectory of a channel of an adjustable turret made using a trajectory guide may be performed manually or automatically with the choice of manual or automatic adjusting being dependent on a number of factors including but not limited to e.g., the level accuracy necessary, whether the adjustment is made manually or automatically, the number of adjustments likely to be performed (e.g., during a particular targeting session), etc.

Manual determinations of the trajectory of a channel of an adjustable turret may be performed by a variety of approaches. In one embodiment, on a computer displayed or printed image of the MRI-visible style the path of the MRI-visible style is traced to determine the trajectory. In some instances, to determine the difference between a determined trajectory and a desired trajectory two lines are drawn: one defined by the path of the MRI-visible style and the other defined by the target and rounded end of the adjustable turret. The angle between the two lines is determined, e.g., through the use of a measuring device e.g., a protractor, or through computer assisted measuring, e.g., software programming that measures the angle, to determine the difference between the determined trajectory and the desired trajectory.

In some instances, determination of the trajectory of a channel of an adjustable turret may be automated. For example, a processor may be programmed to recognize the MRI-visible style from a digital MRI image and automatically plot the trajectory of the style. The plotted trajectory may or may not be displayed on the digital MRI image. In some instances, the automatically plotted trajectory is displayed on a digital MRI image such that a user may make a determination as to whether the plotted trajectory achieves the desired trajectory (e.g., targets the desired area, avoids one or more obstacles, etc.). A user may, in some instances, provide an input to the computer system to indicate whether a desired trajectory and/or what adjustment may be necessary to achieve a desired trajectory.

In some instances, an automatically plotted trajectory is automatically analyzed according to instructions programmed into the computer system to determine whether a desired trajectory is achieved. For example, a user may provide an input representing a desired target area or one or more obstacles to be avoided and the computer system may automatically calculate the trajectory and automatically determine whether the calculated trajectory targets the desired area and/or avoids one or more obstacles. The computer system may then, following the automatic determination, indicate to the user whether the calculated trajectory is sufficient and, if not, the computer system may or may not be further programmed to suggest an adjustment to the trajectory sufficient to target the desired area and/or avoid one or more obstacles. In some instances, an automated system may be further programmed to automatically make the necessary adjustment to achieve a desired trajectory.

As will be readily understood, the above described trajectory determinations, whether manual or automated, may be equally applied in some instances to a plurality of trajectories. Multiple trajectories may be determined in series, i.e., one after the other, e.g., where a process of determining a trajectory of a channel, making an adjustment and re-determining the trajectory is repeated, e.g., until a desired trajectory of the channel is achieved. In some instances, multiple trajectories of a plurality of channels may be determined in parallel, i.e., essentially simultaneously. For example, where a trajectory guide having a plurality of MRI-visible styles is employed, the trajectory of two or more channels may be determined at one time based on two or more styles, including all of the styles, of the plurality.

Figure 3:
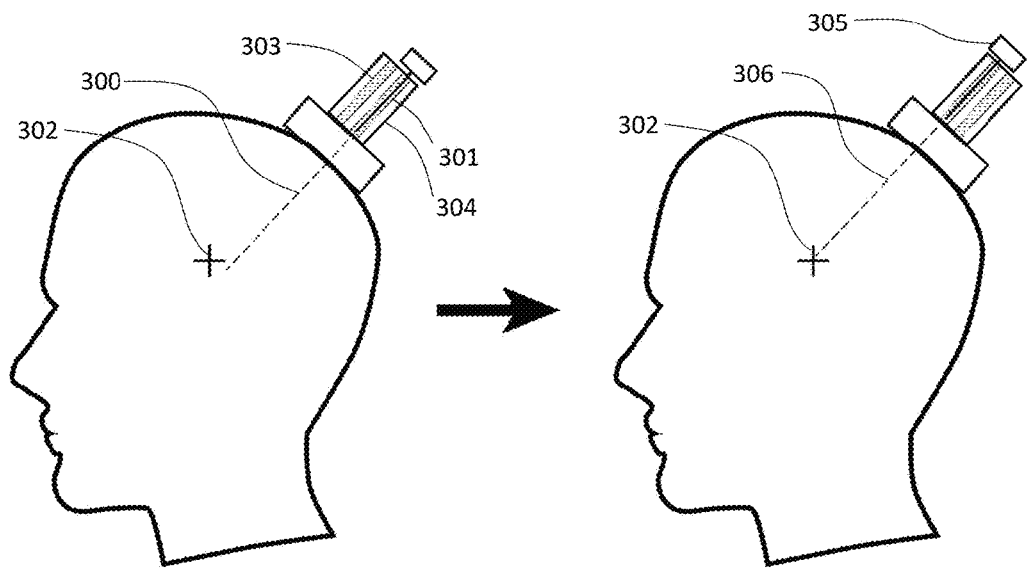
FIG. 3 depicts channel selection of a multi-channel targeting device according to an embodiment of the method described herein.

In some instances, e.g., when multiple trajectories for a plurality of channels are determined, the targeting of a device may be modified by choosing one channel over another based on comparing the determined trajectories of the channels. For example, as depicted in FIG. 3, the trajectory (300) of a first channel (301) may be determined and that the trajectory does not sufficiently target a desired area of a subject's brain (302) may be recognized. At which point a second channel (303) of the adjustable turret (304) may be investigated to determine if it achieves a desired trajectory to the target area. Accordingly, the targeting guide (305) may be moved to the second channel (303) and the trajectory (306) of the second channel may be determined. Where the second channel trajectory (306) is sufficient to target the desired area of the subject's brain (302) then the second channel may be chosen and no further adjustment, e.g., of the adjustable turret, may be necessary. Alternatively, in some instances, neither channel may directly target the desired area and thus the channel having the trajectory that most closely targets the desired area may be chosen and further adjustment of the adjustable turret may be employed to refine the targeting.

As will be readily understood, where an adjustable turret having a plurality of channels and a trajectory guide having a plurality of MRI-visible styles are employed, removing the style from a first channel and placing the style into a second channel, as described in the above embodiment, may not be necessary essentially because some or all of the plurality of channels may simultaneously contain MRI-visible styles allowing for parallel determinations of channel trajectory to be performed. Accordingly, in some instances, a plurality of trajectories may be determined in parallel for an adjustable turret having a plurality of channels and the channel having the trajectory that best targets the desired area may be chosen without removing and replacing the trajectory guide.

Channel selection using an adjustable turret having a plurality of channels may be combined with any of the turret adjustments described herein. For example, in some instances, a channel may be selected having a trajectory nearest the desired trajectory and a roll adjustment may be performed to refine the trajectory. In some instances, a channel may be selected having a trajectory nearest the desired trajectory and an angle adjustment may be performed to refine the trajectory. In some instances, a channel may be selected having a trajectory nearest the desired trajectory and a roll and an angle adjustment may be performed to refine the trajectory.

Following the selection of a channel, an adjustment of the turret or a combination thereof, the selected/adjusted trajectory may be verified. Verification of the trajectory may be performed by a variety of means including but not limited to e.g., determining the trajectory using a trajectory guide and plotting the trajectory on a MRI image of the subject. The plotted trajectory may be checked to verify that the desired area is, in fact, targeted, that the plotted trajectory avoids any obstacles, etc. Where verification confirms that the plotted trajectory is, in fact, a sufficient or desired trajectory then the device may be considered to be sufficiently targeted and downstream uses of the targeted device may be performed. Where verification is unable to confirm that the plotted trajectory is sufficient then iterative adjustments may be employed until a desired trajectory is achieved.

At various points within the method, the position of the adjustable turret may be locked to prevent further adjustment. For example, in some instances, the adjustable turret may be locked in its initial position, e.g., before the initial trajectory of one or more channels is determined. In some instances, the position of the adjustable turret may be locked following adjustment and/or when a trajectory of a channel of the adjustable turret is verified as sufficiently targeted. Locking of the adjustable turret will generally include placing the adjustable turret in a state that does not allow for further adjustment, either angle adjustment and/or roll adjustment, of the turret under normal conditions. In some instances, locking of the turret may involve the use of a locking collar, as described in more detail below, including but not limited to e.g., a locking collar that compresses the round end of the adjustable turret between the base and the locking collar, thus preventing movement.

As briefly discussed above, at various points in the herein described methods the MRI-visible style(s) of the trajectory guide may be removed from the channel(s) of the adjustable turret and/or replaced as desired. Generally, the position of the adjustable turret may be locked prior to removing the MRI-visible style(s), e.g., to maintain a determined trajectory. After channel selection, turret adjustment or combinations thereof to identify or arrive at a sufficient or desired trajectory, the MRI-visible styles will generally be removed to allow access to the targeted channel and insertion of a device into the targeted channel, e.g., as part of a therapeutic method making use of the targeting device.

Therapeutic Methods

Aspects of instant methods include, in some instances, magnetic resonance imaging (MRI)-assisted delivery to a desired area of a subject using one or more targeted channels of a targeting device as described above. Any desired therapeutic agent or therapeutic device may be targeted and delivered to a desired area of a subject according to the methods described herein. Non-limiting examples of agents and therapeutic devices that may be delivered through a targeted channel as described herein include but are not limited to e.g., drugs, nanoparticles, biological agents (e.g., cells, virus, etc.), electrical probes (e.g., electrodes), thermal probes (e.g., heat probes, cold probes, etc.), imaging devices (e.g., endoscopes, lights, etc.), surgical implements, and the like.

Subjects to which the methods of the instant disclosure are applicable include veterinary subjects (e.g., dogs, cats, horses, etc.) and research animal subjects (e.g., mice, rats, rabbits, pigs, goats, sheep, primates, etc.) as well as human subjects. The methods of the invention are applicable to all primates, including e.g., simians. In some embodiments the methods are applied to humans. In other embodiments the methods are applied to non-human primates.

A primate is a member of the biological order Primates, the group that contains lemurs, the Aye-aye, lorisids, galagos, tarsiers, monkeys, and apes, with the last category including great apes. Primates are divided into prosimians and simians, where simians include monkeys and apes. Simians are divided into two groups: the platyrrhines or New World monkeys and the catarrhine monkeys of Africa and southeastern Asia. The New World monkeys include the capuchin, howler and squirrel monkeys, and the catarrhines include the Old World monkeys such as baboons and macaques and the apes.

Any desired area of a subject may be targeted according to the methods described herein. In some instances, the desired area may a tissue, including but not limited to a tissue of endodermal origin, a tissue of ectodermal origin, a tissue mesodermal origin. Both neural and non-neural tissues may be targeted. In some instances, neural tissues of the central nervous system (CNS) may be targeted including e.g., tissues of the brain and tissues of the spinal cord. In some instances, neural tissues of the peripheral nervous system may be targeted.

Non-neural tissues that may be targeted include but are not limited to the skin/epidermis, tissues of the eye, tissues of the olfactory system, tissues of the ear (including inner and outer ear), tissues of the mouth and throat, non-neural tissues of the neck (including e.g., muscles, connective tissues, etc.), tissues of the heart, tissues of the lungs, tissues of stomach, tissues of the intestine (e.g., small intestine, large intestine, colon, etc.), tissues of the liver, tissues of the kidney, tissues of the endocrine system, tissues of the lymphatic system, tissues of the bone (including e.g., the bone marrow), tissues of the vascular system (e.g., arteries, veins, etc.), tissues of the pancreas, tissues of the arms and legs (e.g., muscles, connective tissues in the joints, etc.).

In some instances, the methods of the instant application may be applied for effective delivery/localization of an agent to a region of interest in the mammalian nervous system, including the central nervous system or the peripheral nervous system. Essentially any region of interest of the nervous system may be targeted according to the methods as described herein, including but not limited to e.g., the brain, the spinal cord, the spinal ganglia, etc.

In some instances, the methods of the instant application may be applied for effective delivery/localization of an agent to a region of interest in the mammalian brain. Essentially any region of interest of the brain may be targeted according to the methods as described herein.

In some instances, one or more brain lobes or a particular area within a brain lobe may be targeted, including but not limited to e.g., the frontal lobe (either the entire frontal lobe or portions thereof including but not limited to e.g., Superior Frontal, Rostral Middle Frontal, Caudal Middle Frontal, Pars Opercularis, Pars Triangularis, and Pars Orbitalis, Lateral Orbitofrontal, Medial Orbitofrontal, Precentral, Paracentral, Frontal Pole, combinations thereof, and the like), parietal lobe (either the entire parietal lobe or portions thereof including but not limited to e.g., Superior Parietal, Inferior Parietal, Supramarginal, Postcentral, Precuneus, combinations thereof, and the like), temporal lobe (either the entire temporal lobe or portions thereof including but not limited to e.g., Superior Temporal, Middle Temporal, Inferior Temporal, Banks of the Superior Temporal Sulcus, Fusiform, Transverse Temporal, Entorhinal, Temporal Pole, Parahippocampal, combinations thereof, and the like) and occipital lobe (either the entire occipital lobe or portions thereof including but not limited to e.g., Lateral Occipital, Lingual, Cuneus, Pericalcarine, combinations thereof, and the like).

In some instances, one or more brain structures or a particular area within a brain structure may be targeted including but not limited to e.g., Hindbrain structures (e.g., Myelencephalon structures (e.g., Medulla oblongata, Medullary pyramids, Olivary body, Inferior olivary nucleus, Respiratory center, Cuneate nucleus, Gracile nucleus, Intercalated nucleus, Medullary cranial nerve nuclei, Inferior salivatory nucleus, Nucleus ambiguous, Dorsal nucleus of vagus nerve, Hypoglossal nucleus, Solitary nucleus, etc.), Metencephalon structures (e.g., Pons, Pontine cranial nerve nuclei, chief or pontine nucleus of the trigeminal nerve sensory nucleus (V), Motor nucleus for the trigeminal nerve (V), Abducens nucleus (VI), Facial nerve nucleus (VII), vestibulocochlear nuclei (vestibular nuclei and cochlear nuclei) (VIII), Superior salivatory nucleus, Pontine tegmentum, Respiratory centres, Pneumotaxic centre, Apneustic centre, Pontine micturition center (Barrington's nucleus), Locus coeruleus, Pedunculopontine nucleus, Laterodorsal tegmental nucleus, Tegmental pontine reticular nucleus, Superior olivary complex, Paramedian pontine reticular formation, Cerebellar peduncles, Superior cerebellar peduncle, Middle cerebellar peduncle, Inferior cerebellar peduncle, Fourth ventricle, Cerebellum, Cerebellar vermis, Cerebellar hemispheres, Anterior lobe, Posterior lobe, Flocculonodular lobe, Cerebellar nuclei, Fastigial nucleus, Interposed nucleus, Globose nucleus, Emboliform nucleus, Dentate nucleus, etc.)), Midbrain structures (e.g., Tectum, Corpora quadrigemina, inferior colliculi, superior colliculi, Pretectum, Tegmentum, Periaqueductal gray, Parabrachial area, Medial parabrachial nucleus, Lateral parabrachial nucleus, Subparabrachial nucleus (Kölliker-Fuse nucleus), Rostral interstitial nucleus of medial longitudinal fasciculus, Midbrain reticular formation, Dorsal raphe nucleus, Red nucleus, Ventral tegmental area, Substantia nigra, Pars compacta, Pars reticulata, Interpeduncular nucleus, Cerebral peduncle, Crus cerebri, Mesencephalic cranial nerve nuclei, Oculomotor nucleus (III), Trochlear nucleus (IV), Mesencephalic duct (cerebral aqueduct, aqueduct of Sylvius), etc.), Forebrain structures (e.g., Diencephalon, Epithalamus structures (e.g., Pineal body, Habenular nuclei, Stria medullares, Taenia thalami, etc.) Third ventricle, Thalamus structures (e.g., Anterior nuclear group, Anteroventral nucleus (aka ventral anterior nucleus), Anterodorsal nucleus, Anteromedial nucleus, Medial nuclear group, Medial dorsal nucleus, Midline nuclear group, Paratenial nucleus, Reuniens nucleus, Rhomboidal nucleus, Intralaminar nuclear group, Centromedial nucleus, Parafascicular nucleus, Paracentral nucleus, Central lateral nucleus, Central medial nucleus, Lateral nuclear group, Lateral dorsal nucleus, Lateral posterior nucleus, Pulvinar, Ventral nuclear group, Ventral anterior nucleus, Ventral lateral nucleus, Ventral posterior nucleus, Ventral posterior lateral nucleus, Ventral posterior medial nucleus, Metathalamus, Medial geniculate body, Lateral geniculate body, Thalamic reticular nucleus, etc.), Hypothalamus structures (e.g., Anterior, Medial area, Parts of preoptic area, Medial preoptic nucleus, Suprachiasmatic nucleus, Paraventricular nucleus, Supraoptic nucleus (mainly), Anterior hypothalamic nucleus, Lateral area, Parts of preoptic area, Lateral preoptic nucleus, Anterior part of Lateral nucleus, Part of supraoptic nucleus, Other nuclei of preoptic area, median preoptic nucleus, periventricular preoptic nucleus, Tuberal, Medial area, Dorsomedial hypothalamic nucleus, Ventromedial nucleus, Arcuate nucleus, Lateral area, Tuberal part of Lateral nucleus, Lateral tuberal nuclei, Posterior, Medial area, Mammillary nuclei (part of mammillary bodies), Posterior nucleus, Lateral area, Posterior part of Lateral nucleus, Optic chiasm, Subfornical organ, Periventricular nucleus, Pituitary stalk, Tuber cinereum, Tuberal nucleus, Tuberomammillary nucleus, Tuberal region, Mammillary bodies, Mammillary nucleus, etc.), Subthalamus structures (e.g., Thalamic nucleus, Zona incerta, etc.), Pituitary gland structures (e.g., neurohypophysis, Pars intermedia (Intermediate Lobe), adenohypophysis, etc.), Telencephalon structures, white matter structures (e.g., Corona radiata, Internal capsule, External capsule, Extreme capsule, Arcuate fasciculus, Uncinate fasciculus, Perforant Path, etc.), Subcortical structures (e.g., Hippocampus (Medial Temporal Lobe), Dentate gyrus, Cornu ammonis (CA fields), Cornu ammonis area 1, Cornu ammonis area 2, Cornu ammonis area 3, Cornu ammonis area 4, Amygdala (limbic system) (limbic lobe), Central nucleus (autonomic nervous system), Medial nucleus (accessory olfactory system), Cortical and basomedial nuclei (main olfactory system), Lateral[disambiguation needed] and basolateral nuclei (frontotemporal cortical system), Claustrum, Basal ganglia, Striatum, Dorsal striatum (aka neostriatum), Putamen, Caudate nucleus, Ventral striatum, Nucleus accumbens, Olfactory tubercle, Globus pallidus (forms nucleus lentiformis with putamen), Subthalamic nucleus, Basal forebrain, Anterior perforated substance, Substantia innominata, Nucleus basalis, Diagonal band of Broca, Medial septal nuclei, etc.), Rhinencephalon structures (e.g., Olfactory bulb, Piriform cortex, Anterior olfactory nucleus, Olfactory tract, Anterior commissure, Uncus, etc.), Cerebral cortex structures (e.g., Frontal lobe, Cortex, Primary motor cortex (Precentral gyrus, M1), Supplementary motor cortex, Premotor cortex, Prefrontal cortex, Gyri, Superior frontal gyrus, Middle frontal gyrus, Inferior frontal gyrus, Brodmann areas: 4, 6, 8, 9, 10, 11, 12, 24, 25, 32, 33, 44, 45, 46, 47, Parietal lobe, Cortex, Primary somatosensory cortex (S1), Secondary somatosensory cortex (S2), Posterior parietal cortex, Gyri, Postcentral gyrus (Primary somesthetic area), Other, Precuneus, Brodmann areas 1, 2, 3 (Primary somesthetic area); 5, 7, 23, 26, 29, 31, 39, 40, Occipital lobe, Cortex, Primary visual cortex (V1), V2, V3, V4, V5/MT, Gyri, Lateral occipital gyrus, Cuneus, Brodmann areas 17 (V1, primary visual cortex); 18, 19, Temporal lobe, Cortex, Primary auditory cortex (A1), secondary auditory cortex (A2), Inferior temporal cortex, Posterior inferior temporal cortex, Superior temporal gyrus, Middle temporal gyrus, Inferior temporal gyrus, Entorhinal Cortex, Perirhinal Cortex, Parahippocampal gyrus, Fusiform gyrus, Brodmann areas: 9, 20, 21, 22, 27, 34, 35, 36, 37, 38, 41, 42, Medial superior temporal area (MST), Insular cortex, Cingulate cortex, Anterior cingulate, Posterior cingulate, Retrosplenial cortex, Indusium griseum, Subgenual area 25, Brodmann areas 23, 24; 26, 29, 30 (retrosplenial areas); 31, 32, etc.)).

In some instances, one or more neural pathways or a particular portion of a neural pathway may be targeted including but not limited to e.g., neural pathways of those brain lobes and structures described above, Superior Longitudinal Fasciculus, Arcuate fasciculus, Cerebral peduncle, Corpus callosum, Pyramidal or corticospinal tract, Major dopamine pathways dopamine system, Mesocortical pathway, Mesolimbic pathway, Nigrostriatal pathway, Tuberoinfundibular pathway, Serotonin Pathways serotonin system, Raphe Nuclei, Norepinephrine Pathways, Locus coeruleus, etc.

In some instances, diseased and/or disease causing tissue may be targeted. Any disease and/or disease causing tissue may be targeted according to the instant methods including but not limited to e.g., diseased neural tissue, solid tumors, neural or CNS tumors, and the like. As used herein, a "CNS tumor" or "tumor of the CNS" refers to a primary or malignant tumor of the CNS of a subject, e.g., the aberrant growth of cells within the CNS. The aberrantly growing cells of the CNS may be native to the CNS or derived from other tissues.

In some instances, targeted tumors may include but are not limited to e.g., gliomas e.g., glioblastoma multiforme (GBM), astrocytoma, including fibrillary (diffuse) astrocytoma, pilocytic astrocytoma, pleomorphic xanthoastrocytoma, and brain stem glioma, oligodendroglioma, ependymoma and related paraventricular mass lesions, neuronal tumors, poorly differentiated neoplasms, including medulloblastoma, other parenchymal tumors, including primary brain lymphoma, germ cell tumors, pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma).

Diseased neural tissues that may be targeted include but are not limited to e.g., neural tissue disease due to one or more of meningitis, encephalitis, multiple sclerosis (MS), stroke, brain tumors, epilepsy, Alzheimer's disease, AIDS related dementia, Parkinson's disease.

The methods of the instant disclosure may be applied to delivery of therapeutic agents to a targeted region of a subject, including e.g., the brain of a subject. Agents of interest include, without limitation, proteins, drugs, antibodies, antibody fragments, immunotoxins, chemical compounds, protein fragments, viruses, nucleic acids (e.g., (expression vectors, gene therapy vectors, small hairpin nucleic acids, interfering nucleic acids, aptamers, etc.) and toxins.

In some instances, the methods of the instant disclosure may include the delivery of a gene therapy vector including but not limited to e.g., delivery of an adenovirus (AAV) gene therapy vector.

In some instances, the methods of the instant disclosure may include the delivery of cell therapies. As used herein, the term "cell therapy" generally includes therapies derived from the delivery of living cells, whether or not recombinantly engineered, to a subject. Useful cells delivered in cell therapies include but are not limited to e.g., stem cells (e.g., adult stem cells (e.g., mesenchymal stem cells, adipose stem cells, muscle satellite cells, neural stem cells, liver stem cells, hematopoietic stem cells, etc.), embryonic stem cells, induced pluripotent stem cells (iPS), etc.) and terminally or partially differentiated cell types. Useful cell types also include e.g., engineered immune cell type such as e.g., engineered T cells.

Therapeutic agents, including cellular therapeutics, are administered according to the methods described herein at any effective concentration. An effective concentration of a therapeutic agent is one that results in decreasing or increasing a particular pharmacological effect. One skilled in the art would know how to determine effective concentration according to methods known in the art, as well as provided herein.

Dosages of the therapeutic agents will depend upon the disease or condition to be treated, and the individual subject's status (e.g., species, weight, disease state, etc.) Dosages will also depend upon how the agents are being administered where precise targeted delivery may in some instances allow for an effective dose that is smaller than a systemic dose or even a dose delivered to the general area (e.g., the brain generally) but not specifically targeted. Effective dosages are known in the art or can be determined empirically. Furthermore, the dosage can be adjusted according to the typical dosage for the specific disease or condition to be treated. Often a single dose can be sufficient; however, the dose can be repeated if desirable. The dosage should not be so large as to cause adverse side effects. Generally, the dosage will vary with the age, condition, sex and extent of the disease in the patient and can be determined by one of skill in the art according to routine methods (see e.g., Remington's Pharmaceutical Sciences). The dosage can also be adjusted by the individual physician in the event of any complication.

The therapeutic agent can typically include an effective amount of the respective agent in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected agent without causing any undesirable biological effects or interacting in a deleterious manner with any of the other components of the pharmaceutical composition in which it is contained.

For the delivery of a therapeutic agent according to the instant methods, generally a targeting device will be targeted to a desired area as described above using a targeting guide. Following targeting, the targeting guide may be removed, removing the style(s) from the channel(s) of the targeted device and replacing one or more styles with a therapeutic delivery device. Once in place within the channel of the targeting device the therapeutic delivery device may be deployed and/or activated, e.g., to cause the therapeutic to be released, injected, dispersed, etc. Following delivery, the delivery device may be removed or may be left in place, e.g., where a dosage protocol calls for repeated dosing. In some instances, following one or more doses, the targeting device may remain in place and targeting may be checked, and adjusted if necessary, using a targeting guide prior to subsequent dosing.

The subject methods are not limited to therapeutic delivery and also include targeted surgical applications such as e.g., targeted cell ablation, targeted electrical stimulation, etc. In some instances, a targeting device may be applied as described herein to direct a probe, e.g., an ablation probe, an electrode, etc., to a desired area of the subject and the probe may be activated to provide for targeted ablation (e.g., targeted neuroablation), targeted stimulation (e.g., targeted neurostimulation), etc.

The subject methods are not limited to therapeutic delivery and surgical applications and also include targeted diagnostics. In some instances, a diagnostic device may be deployed through a targeting device according to the methods as described herein for precise diagnostic protocols. For example, in some instances, a biopsy collection device (e.g., a fine needle aspirate device) may be applied using a targeting system and method described herein to precisely target and collect a desired biopsy. In some instances, a diagnostic imaging instrument, e.g., an endoscope, may be applied using a targeting system and method described herein to precisely target and collect a desired image for diagnostic purposes. Useful endoscopes include but are not limited to e.g., those commercially available from Medigus Ltd (Omer, Israel) including but not limited to e.g., the micro ScoutCam endoscope cameras.

Devices and Systems

The instant disclosure provides devices and systems useful in methods for targeting a biomedical device or therapy to a desired area of a subject, including devices and systems useful in practicing those methods as described herein. Devices described herein include trajectory guides, adjustable turret targeting systems, and components thereof. In some instances, the described systems may include imaging devices, biomedical systems, etc. The described devices, systems and components thereof may, as appropriate, be manually controlled or fully or partially automated as described in more detail herein.

In some instances, the herein described devices, or components thereof, may serve as a holder for therapeutic administration devices including but not limited to e.g., drug delivery devices, viral vector delivery devices, nanoparticle delivery devices, cell administration delivery devices, cell delivery devices, and the like.

The instant disclosure includes trajectory guides. Trajectory guides of the instant disclosure will generally include at least one MRI-visible style attached to base, where imaging the MRI-visible style allows for the determination of the trajectory of a device into which the MRI-visible style is placed. MRI-visible styles of a trajectory guide may be flexible, rigid or semi-rigid, depending on the particular context. A MRI visible style may, in some instances, be constructed from a tube, including flexible tubes and rigid tubing, and may have a cap at the distal end and be open or closed at the proximal end attached to the base. A cavity or lumen within the MRI-visible style may facilitate filling the MRI-visible style with a contrast agent. In some instances, other configurations of an MRI-visible style may be employed including e.g., where the MRI-visible style is constructed of an MRI-visible material, including e.g., a material embedded with an MRI-contrast agent, with or without a coating.

Any convenient MRI contrast agent may find use in MRI-styles described herein including but not limited solid (e.g., particle), liquid and gel contrast agents. Accordingly, depending on the application, e.g., whether the style is rigid or flexible, contrast agents used may vary and may include but are not limited to e.g., Gadolinium(III) containing MRI contrast agents (e.g., gadobenate, gadobutrol, gadocoletic acid, gadodiamide, gadofosveset, gadomelitol, gadomer 17, gadopentetate, gadopentetic acid dimeglumine, gadoterate, gadoteridol, gadoversetamide, gadoxetate, gadoxeticacid, etc.), iron oxide containing MRI contrast agents (e.g., Feridex, Resovist, Sinerem, Lumirem, PEG-fero (a.k.a., Feruglose), etc.), iron platinum containing MRI contrast agents (e.g., iron-platinum-based nanoparticles), manganese containing MRI contrast agents (e.g., Mn-based nanoparticles), and the like.

Referring now to FIG. 6A, in one embodiment, a trajectory guide of the instant disclosure may include a single MRI-visible style (600) attached to a base (601). The base of the trajectory guide will generally have a surface, e.g., a flat surface or an essentially flat surface, to which one or more MRI-visible styles at attached. In some instances, the surface may contain one or more holes or one or more wells into which the one or more styles may be inserted. In the embodiment depicted, the MRI-visible style is constructed of a tube having a cap at the distal end (602), allowing the tube to be filled with a contrast agent. As can be seen in the cross-sectional depiction in FIG. 6B, the MRI-visible style (600) has an internal lumen (603) which may be filled, e.g., with an MRI-visible contrast agent. In some instances, the base may include a void or cavity (604) that is contiguous or confluent with the lumen of the MRI-visible style (603), e.g., by a direct connection of the void and lumen or by means of an intermediate connection such as, e.g., a passage (605) as depicted in FIG. 6B.

In some instances, trajectory guides of the instant disclosure may include a plurality of MRI-visible styles, e.g., as present in the embodiment depicted in FIG. 7A, which includes a base (700) and seven MRI-visible styles (701) attached orthogonally to the base. The actual number of MRI-visible styles may vary depending on a number of factors including but not limited to e.g., the overall size of the trajectory guide, the dimensions of the targeting device to which the trajectory guide is made compatible, the requirements of the desired targeting application and the like. As such, the number of MRI-visible styles of a targeting guide may range from 1 to 64 or more including but not limited to e.g., 1 to 64, 1 to 55, 1 to 50, 1 to 45, 1 to 40, 1 to 36, 1 to 30, 1 to 24, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 4, 1 to 3, 2 to 64, 2 to 55, 2 to 50, 2 to 45, 2 to 40, 2 to 36, 2 to 30, 2 to 24, 2 to 20, 2 to 19, 2 to 18, 2 to 17, 2 to 16, 2 to 15, 2 to 14, 2 to 13, 2 to 12, 2 to 11, 2 to 10, 2 to 9, 2 to 8, 2 to 7, 2 to 6, 2 to 5, 2 to 4, 5 to 64, 5 to 55, 5 to 50, 5 to 45, 5 to 40, 5 to 36, 5 to 30, 5 to 24, 5 to 20, 5 to 19, 5 to 18, 5 to 17, 5 to 16, 5 to 15, 5 to 14, 5 to 13, 5 to 12, 5 to 11, 5 to 10, 5 to 9, 5 to 8, 5 to 7, 10 to 64, 10 to 55, 10 to 50, 10 to 45, 10 to 40, 10 to 36, 10 to 30, 10 to 24, 10 to 20, 10 to 19, 10 to 18, 10 to 17, 10 to 16, 10 to 15, 10 to 14, 10 to 13, 10 to 12, 12, 11, 10, 9, 8, 7, 6, 5, 4, 3, 2, 1, etc.

The trajectory guide embodiment of FIG. 7A, is further depicted in FIG. 7B, but with the closeable cap (703) removed. Removal of the cap (703) may allow access to a cavity in the base (704) allowing for the filling and/or replacing of contrast agent. The cap may be affixed to the base by any suitable means including e.g., a compression fitting or, as depicted compatible threading in the cap (705) and base (706). Furthermore, the trajectory guide may or may not make use of one or more gaskets or O-rings, such as e.g., the gasket (707) depicted in FIG. 7B that provides a seal between the cap and base to prevent leakage of the contrast agent. In some instances, component parts of a trajectory guide may be machined such that a gaskets and/or O-rings are not necessary.

In some instances, the trajectory guide may not include a removable cap. For example, in some embodiments the trajectory guide may be configured such that access to one or more lumens of one or more MRI-visible styles is unnecessary and such configurations may not include a removable cap or may not otherwise provide access to the lumen(s) of the MRI-visible styles. In some instances, where an MRI-visible style does not include a removable cap on the base, access to the lumen of the MRI-visible style(s) may be achieved through one or more removable caps on the distal end of the MRI-visible styles. Depending on the particular configuration and the MRI contrast agent employed, in some instances, the contrast agent may need to be periodically replaced and in other instances the MRI-contrast agent may not need to be replaced.

The MRI-visible style(s) of a trajectory guide may vary in size along various dimensions, including e.g., length, width, diameter, etc., and may, in some instances, be configured and/or dimensioned for insertion into a channel of an adjustable turret of a targeting device, as described in more detail below. For example, the length of the MRI-style, as measured from the base of the targeting guide to the distal end, may be essentially the same as the length of the channel into which it is inserted or shorter. The gauge of the MRI-style may be dimensioned such that the style may be inserted into a channel an adjustable turret of a targeting device to allow for determining the trajectory of the channel. For example, the gauge of the style may be sufficiently large to conform to the trajectory of the channel but also sufficiently small to allow for easy insertion of the style into the channel.

As such, the dimensions of the MRI-visible style(s) of a trajectory guide may vary. In some instances, the length of the MRI-visible style(s) may range from 1 cm or less to 10 cm or more including but not limited to e.g., 1 cm to 10 cm, 2 cm to 10 cm, 3 cm to 10 cm, 4 cm to 10 cm, 5 cm to 10 cm, 1 cm to 9 cm, 1 cm to 8 cm, 1 cm to 7 cm, 1 cm to 6 cm, 1 cm to 5 cm, 2 cm to 5 cm, 3 cm to 6 cm, 2 cm to 4 cm, 3 cm to 5 cm, 1 cm, 2 cm, 3 cm, 4 cm, 5 cm, and the like. In some instances, the gauge of the MRI-visible style(s) may range from 42 gauge or less to 6 gauge or more, according to British Standard Wire Gauge (SWG) measurements, including but not limited to e.g., 42 gauge, 41 gauge, 40 gauge, 39 gauge, 38 gauge, 37 gauge, 36 gauge, 35 gauge, 34 gauge, 33 gauge, 32 gauge, 31 gauge, 30 gauge, 29 gauge, 28 gauge, 27 gauge, 26 gauge, 25 gauge, 24 gauge, 23 gauge, 22 gauge, 21 gauge, 20 gauge, 19 gauge, 18 gauge, 17 gauge, 16 gauge, 15 gauge, 14 gauge, 13 gauge, 12 gauge, 11 gauge, 10 gauge, 9 gauge, 8 gauge, 7 gauge, 6 gauge, and the like.

As described above, the trajectory guide and/or the MRI-visible style(s) thereof may be dimensioned to be compatible with an adjustable turret of the targeting device as described herein. Any portion or component of the trajectory guide and/or MRI-visible style(s) may be dimensioned to be compatible with an adjustable turret including, e.g., the diameter or gauge of the style(s) may be dimensioned to be compatible with the channel(s) of the adjustable turret. In some instances, the channel(s) and style(s) are configured to be compatible in length. In some instances, the base of the trajectory guide is configured to be compatible with a surface of the adjustable turret having the openings to the channels into which the style(s) are inserted. The turret and the trajectory guide need not be compatibly dimensioned in all aspects and, in some instances may differ, e.g., differ in length of the styles and the length of the channels, differ in the size of the flat surface of the base of the trajectory guide and the flat surface of the turret having the channel holes, etc. Provided it does not negatively impact the functioning of the device any corresponding components of the turret and the trajectory guide may or may not be compatible dimensioned.

Aspects of the instant disclosure include an adjustable turret of a targeting device. In general, adjustable turrets of the instant disclosure will include a distal end and rounded end, e.g., a spherical or essentially spherical end. Adjustable turrets as described will also generally include at least one channel running from the distal end to the rounded end allowing for insertion of the style(s) of a trajectory guide for targeting and insertion of one or more biomedical devices for various purposes including e.g., agent delivery, device delivery, imaging, etc. In some instances, an adjustable turret may have a single channel. In other instances, an adjustable turret may have a plurality of channels. As such, the number of channels in an adjustable turret may range, e.g., from 1 to 64 or more including but not limited to e.g., 1 to 64, 1 to 55, 1 to 50, 1 to 45, 1 to 40, 1 to 36, 1 to 30, 1 to 24, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 4, 1 to 3, 2 to 64, 2 to 55, 2 to 50, 2 to 45, 2 to 40, 2 to 36, 2 to 30, 2 to 24, 2 to 20, 2 to 19, 2 to 18, 2 to 17, 2 to 16, 2 to 15, 2 to 14, 2 to 13, 2 to 12, 2 to 11, 2 to 10, 2 to 9, 2 to 8, 2 to 7, 2 to 6, 2 to 5, 2 to 4, 5 to 64, 5 to 55, 5 to 50, 5 to 45, 5 to 40, 5 to 36, 5 to 30, 5 to 24, 5 to 20, 5 to 19, 5 to 18, 5 to 17, 5 to 16, 5 to 15, 5 to 14, 5 to 13, 5 to 12, 5 to 11, 5 to 10, 5 to 9, 5 to 8, 5 to 7, 10 to 64, 10 to 55, 10 to 50, 10 to 45, 10 to 40, 10 to 36, 10 to 30, 10 to 24, 10 to 20, 10 to 19, 10 to 18, 10 to 17, 10 to 16, 10 to 15, 10 to 14, 10 to 13, 10 to 12, 12, 11, 10, 9, 8, 7, 6, 5, 4, 3, 2, 1, etc.

The size of the rounded end of the adjustable turret may vary. For example, in some instances, an essentially spherical rounded end of an adjustable turret may range from 1 cm to 10 cm or more in diameter including but not limited to e.g., from 1 cm to 10 cm, from 2 cm to 10 cm, from 3 cm to 10 cm, from 4 cm to 10 cm, from 5 cm to 10 cm, from 6 cm to 10 cm, from 7 cm to 10 cm, from 8 cm to 10 cm, from 9 cm to 10 cm, from 1 cm to 9 cm, from 1 cm to 8 cm, from 1 cm to 7 cm, from 1 cm to 6 cm, from 1 cm to 5 cm, from 1 cm to 4 cm, from 1 cm to 3 cm, from 1 cm to 2 cm, etc. Similarly, the length, along the long axis, of the adjustable turret will also vary where such length will also correspond or nearly correspond to the length of one or more channels of the turret. In some instances, the length of the adjustable turret may range from 1 cm or less to 10 cm or more including but not limited to e.g., from 1 cm to 10 cm, from 2 cm to 10 cm, from 3 cm to 10 cm, from 4 cm to 10 cm, from 5 cm to 10 cm, from 6 cm to 10 cm, from 7 cm to 10 cm, from 8 cm to 10 cm, from 9 cm to 10 cm, from 1 cm to 9 cm, from 1 cm to 8 cm, from 1 cm to 7 cm, from 1 cm to 6 cm, from 1 cm to 5 cm, from 1 cm to 4 cm, from 1 cm to 3 cm, from 1 cm to 2 cm, from 2 cm to 9 cm, from 2 cm to 8 cm, from 2 cm to 7 cm, from 2 cm to 6 cm, from 2 cm to 5 cm, from 2 cm to 4 cm, from 3 cm to 9 cm, from 3 cm to 8 cm, from 3 cm to 7 cm, from 3 cm to 6 cm, from 3 cm to 5 cm, from 3 cm to 4 cm, etc. The difference in size of the distal end of the turret and the rounded end of the turret will also vary. For example, where the rounded end is essentially spherical and the distal end is essentially cylindrical, the ratio between the largest diameter at the spherical end and the diameter of the cylinder may range from more than 10:1 to than 1:1 including but not limited to e.g., 10:1, 9:1, 8:1, 7:1, 6:1, 5:1, 4:1, 3:1, 2:1, and the like.

An adjustable turret may or may not be configured to have the same number of channels as a corresponding trajectory guide. In addition, an adjustable turret may or may not be configured such that the channel(s) of the trajectory guide are in the same configuration as the style(s) of the trajectory guide. Accordingly, all, some or any one channel of an adjustable turret may be symmetrically or asymmetrically arranged with respect to the geometric center of the distal surface of the trajectory guide, i.e., the surface having the opening(s) to the channel(s). Accordingly, all, some or any one style of a trajectory guide may be symmetrically or asymmetrically arranged with respect to the geometric center of the surface to which they are attached, i.e., the surface of the base to which they are attached. In addition, in some instances, the arrangement of channels in an adjustable turret and the arrangement of styles in a corresponding trajectory guide may be configured to be compatible, whether or not the turret contains a channel or channels which are asymmetrically arranged or the trajectory guide contains a style or styles which are asymmetrically arranged.

Any convenient arrangement of channels and/or styles may find use in the methods and devices of the subject disclosure. For simplicity various non-limiting arrangements will be described below in reference to the channels of an adjustable turret; however, it will be readily understood that such arrangement may be equally applied to the styles of a trajectory guide. In embodiments having a single channel, the channel may be arranged in the turret at any convenient location including, e.g., as depicted in FIG. 4A, the channel (400) may be positioned at the geometric center of the turret (401), i.e., coaxial with the long axis of the turret, or the channel (402) may be positioned away from the geometric center (403) of the turret (404), i.e., not coaxial with the long axis of the turret.

As depicted in the non-limiting examples of FIG. 4B, in embodiments having a plurality of channels, two channels of the plurality may be positioned symmetrically with respect to the geometric center of the turret (405), or may be equidistant from the geometric center of the turret but offset from the center (406), or one of the two channels may be positioned at the center of the turret (407). As depicted in the non-limiting examples of FIG. 4C, in embodiments having three or more channels, three of the channels may be positioned symmetrically about the geometric center of the turret (408), or asymmetrically about the geometric center of the turret (409), or one of the three may be positioned at the center of the turret (410).

Further exemplary depictions of possible arrangements of channels are provided for turrets having four channels (FIG. 4D), five channels (FIG. 4E) and six or more channels (FIG. 5F). It will be understood, that the examples provided are not intended to be limiting as to the arrangement of channels, and correspondingly, to the arrangement of styles. It will be understood that such arrangements may vary greatly and be configured and reconfigured according to the particular desired use of the subject targeting system. Furthermore, although described above with regard to the geometric center of the turret, the symmetry of the arrangement of channels and/or styles may be referred to relative to any other component of aspect thereof of the system including e.g., another channel or channels of the system, another style or styles of the system, any axis, plane or center of a surface of a component of the system, etc.

The channel(s) of the adjustable turret and/or the style(s) of the trajectory guide may or may not be arranged parallel to the long axis of the turret or guide, respectively. Similarly, the channels of an adjustable turret having a plurality of channels may or may not be arranged parallel to one another and/or the styles of a trajectory guide having a plurality of styles may or may not be arranged parallel to one another. In some instances, e.g., as depicted in FIG. 5A, the channels (500) of an adjustable turret (501) may be configured parallel to the long axis of the adjustable turret such that their trajectories remain essentially parallel. In some instances, e.g., as depicted in FIG. 5B, the channels (502) of an adjustable turret (503) may be configured such that they are not parallel, either to the long axis of the adjustable turret or one another or both, and their trajectories are correspondingly not parallel.

In some instances, a channel that is arranged within an adjustable turret not parallel to the long axis of the adjustable turret may be referred to as flared and/or having a flared trajectory. As used herein the term "flared" will generally refer to a trajectory, e.g., of a channel or style, that is not parallel with the long axis of the device to which it is attached and having an acute angle relative to the long axis. Components of the subject devices may be flared to various magnitudes, e.g., as measured by the angle of deviation from the long axis of the device. For example in some instances a component, e.g., a channel or a style, may be flared by 1 degree or more, including but not limited to e.g., 2 degrees or more, 3 degrees or more, 4 degrees or more, 5 degrees or more, 6 degrees or more, 7 degrees or more, 8 degrees or more, 9 degrees or more, 10 degrees or more, 15 degrees or more, 20 degrees or more, etc., but generally not flared more than about 40 degrees. A device may but need not have only parallel or flared components and, as such, in some instances parallel and flared components may be combined.

Turning now to the adjustable turret depicted in FIG. 8A. In the depicted embodiment, the adjustable turret has essentially a spherical portion (800) and a cylindrical portion (801) and a plurality of channels (802) running from the flat surface on the distal end (803) of the cylindrical portion to the opposite end on the spherical portion. The rounded portion of the adjustable turret may or may not have a flat surface corresponding to the point at which the channels exit the turret. For example, as depicted in FIG. 8B, in some instances, a spherical end (804) of an adjustable turret has a flat surface (805) at that contains the channel openings (806).

In some instances, the adjustable turret may include one or more means for securing items inserted into one or more of the channels. For example, as depicted in the embodiment of FIGS. 8A and 8B, an adjustable turret may include one or more screws (807) and corresponding screw holes that extend into one or more channels such that, when tightened, the screws secure within the channel any device or other component that has been inserted into the channel. Correspondingly, e.g., when the device or other component is to be removed, the screw or other fastener may be loosened allowing removal.

In some instances, all or a portion of the adjustable turret may be made to be MRI-visible, e.g., by embedding a contrast agent in the adjustable turret, by filling a cavity of the adjustable turret with a contrast agent, etc. In some instances, where all or a portion of the adjustable turret is made to be MRI-visible the MRI-visible portion of the adjustable turret may serve the targeting purposes of the herein described MRI-visible style. For example, where the entire adjustable turret is made to be MRI-visible, visualizing the turret with an MRI device may allow for a determination of trajectory and/or trajectory adjustments. In another example, where the adjustable turret includes an MRI-visible portion or an embedded MRI-visible element or a cavity filled with a contrast agent that is parallel with one or more channels of the adjustable turret, the MRI-visible portion or embedded MRI-visible element or cavity filled with contrast agent may allow for a determination of trajectory and/or trajectory adjustments. In one embodiment, an adjustable turret as described herein may include an MRI-visible portion along the long-axis of the adjustable turret parallel with and/or adjacent to one or more channels of the adjustable turret.

MRI-visible portions along the long-axis of an adjustable turret may vary in length and may e.g., run the entire length of the adjustable turret, less that the entire length of the adjustable turret, more than half of the length of the adjustable turret, about half of the length of the adjustable turret, less than half the length of the adjustable turret, about 100% of the length of the adjustable turret, from about 90% to about 100% of the length of the adjustable turret, from about 50% to about 100% of the length of the adjustable turret, from about 75% to about 100% of the length of the adjustable turret, about 50% of the length of the adjustable turret, from about 10% to about 50% of the length of the adjustable turret, from about 25% to about 50% of the length of the adjustable turret, from about 25% to about 75% of the length of the adjustable turret, from about 10% to about 90% of the length of the adjustable turret, about 10% of the length of the adjustable turret, and the like.

In some instances, an adjustable turret of the instant disclosure may include an MRI-visible band. By "MRI-visible band", as used herein, is meant a circular or semi-circular or elliptical strip of MRI-visible material (including e.g., a cavity filled with a contrast agent) that encircles the circumference or a portion thereof (including e.g., half of, or a majority thereof, etc.) of the adjustable turret. An MRI-visible band may be arranged perpendicular to the long-axis of the adjustable turret. An MRI-visible band may be placed at any position along the long-axis of the adjustable turret. An MRI-visible band may server various functions in determining the position of the adjustable turret or a channel thereof or a device inserted into a channel of the adjustable turret. For example, in some instances, visualization of an MRI-visible band using an MRI imager allows for performing depth calculations related to the position of the adjustable turret or a channel thereof or a device inserted into a channel of the adjustable turret.

As an illustration, in one embodiment, a device is inserted into a channel of an adjustable turret having an MRI-visible band and one end of the device or a specific position along the length of the device is aligned with the band. Next the adjustable turret is MRI imaged and a depth calculation is performed involving a measurement of the distance between a target area and the MRI-visible band. Such a depth calculation may allow a user to determine how much of a device to insert into a channel of an adjustable turret such that the device reaches the desired target area. Other configurations using an MRI-visible band for depth calculation and other purposes will be readily apparent.

The adjustable turret of the instant devices and systems may be configured to be compatible with other components, e.g., for securing the adjustable turret between adjustments and/or securing the adjustable turret to a subject. In some instances, an adjustable turret may be part of a multi-component targeting device, e.g., as depicted in FIG. 9A. In the embodiment of FIG. 9A, the multi-component targeting device has an adjustable turret (900), e.g., as described above, a base component (901) and a locking component (902). As can be seen in FIG. 9B, which provides an exploded version of the embodiment depicted in FIG. 9A, the base component (903) may be configured to receive the rounded end of the adjustable turret (904), e.g., the rounded end of the adjustable turret may "snap into" the base component.

The locking component (905) may be configured to allow the distal end, e.g., the cylindrical end, of the adjustable turret (906) to pass freely through the inner diameter of the locking component. The inner diameter of the locking component will generally be configured to be smaller than the diameter of the rounded end of the adjustable turret (904). Such a configuration of relative sizes will generally allow for the locking component to compress the rounded end of the adjustable turret when the multi-component device is assembled, e.g., by means of compatible threading on the exterior surface of the base (907) and interior surface threading on the locking component (908).

Accordingly, by turning the locking collar one direction, i.e., tightening the locking collar, the round end of the turret is compressed between the locking collar and the base and adjustment of the turret is restricted. Turning the locking collar the opposite direction, i.e., loosening the locking collar, the compression of the round end of the turret between the locking collar and the base is released and adjustment of the turret is possible.

The locking collar need not necessarily contact the round end of the turret to effectively compress the round end of the turret and restrict adjustment. For example, in some instances, the locking collar is configured such that the locking collar contacts only the based and does not contact the round end of the adjustable turret. In such instances, turning the locking collar may compress the base, including but not limited to e.g., a plurality of annular walls of the base as described in more detail below, into the round end of the turret without directly contacting the round end of the turret. As such, in some instances, the smallest inner diameter of the locking collar may be larger than the largest diameter of the round end of the adjustable turret. However, depending on the configuration of the base, including but not limited to e.g., the configuration of the plurality of annular walls of the base, the smallest inner diameter of the locking collar need not necessarily be larger than the largest diameter of the round end of the adjustable turret.

In some instances, the locking collar is configured such that, when the components of the systems are engaged, the locking collar does not or only minimally impacts the maximum turret angle adjustment. Accordingly, even when the components of the device are assembled, significant angle adjustment near the otherwise maximum adjustment of the turret is possible.

In some embodiments, the locking collar may have a lower end that engages the base and an upper end opposite the base where the upper end has a diameter sufficiently large such that, at maximum angle adjustments, the turret does not contact the upper end. For example, as illustrated in FIG. 14C which shows a cutaway of one embodiment of the multicomponent device, the locking collar (1400) has a lower end (1404) that engages the base (1405) and an upper end (1401) that is essentially a ring with an inner diameter (1402) that matches or exceeds the maximum angle adjustment "X" of the turret (1403). Thus, in some instances, the upper end of the locking collar will have a diameter that is larger than the diameter of the lower end of the locking collar.

In some instances, the locking collar may include a flat surface surrounding the upper ring shaped end that is configured for turning the locking collar, i.e., tightening and loosening the locking collar. For example, in the embodiment depicted in FIG. 14A, the locking collar has a flat surface (1406) configured for turning the locking collar. Such flat surfaces may or may not be textured. For example, in some instances the flat surface of the locking collar may be knurled to facilitate grip on the locking collar to facilitate turning the locking collar. Texturing and/or knurling is not limited to the flat surface of the locking collar as described and, in some instances, any other surface of any component of the device may be correspondingly textured and/or knurled to facilitate grip where appropriate.

The individual components of the systems may be configured such that one or more components, including all of the components of the assembled system are substantially ex vivo. In some instances, the base is attached to the subject such that the base remains substantially and/or completely ex vivo. In some instances, the turret is attached to the subject such that the turret remains substantially and/or completely ex vivo. For example, as depicted in FIGS. 14A, and 14B which provides a 90 degree rotated view of the embodiment of FIG. 14A, the assembled unit, attached to a subject at the base (1407), remains on the outside of the subject. In some instances, the base is attached to the subject and the assembled unit is configured such that the rounded end of the turret is positioned substantially flush with the surface of the subject to which the base is attached. Where the turret has a flat surface on the rounded end which contains the channel opening(s) and when the turret is aligned perpendicular to the base, the plane of the flat surface will be substantially parallel or substantially coplanar with the surface of the base that interfaces with the subject.

In instances herein where a component or the system is described as completely or substantially ex vivo such description excludes any fastener(s) that may be inserted into the subject to attach the component or system. Likewise, descriptions of a component or the system being substantially or completely ex vivo will exclude situations where the component of system is normally ex vivo but minimally breaks the plane separating ex vivo space from in vivo space in certain adjustment positions. For example, in some instances, when a maximal angle adjustment is applied to the turret a small portion of the turret may extend toward to the subject beyond the base (see e.g., FIG. 14A and FIG. 14B). However, as described herein such instances are still considered to be substantially and/or completely ex vivo.

Figure 15A:
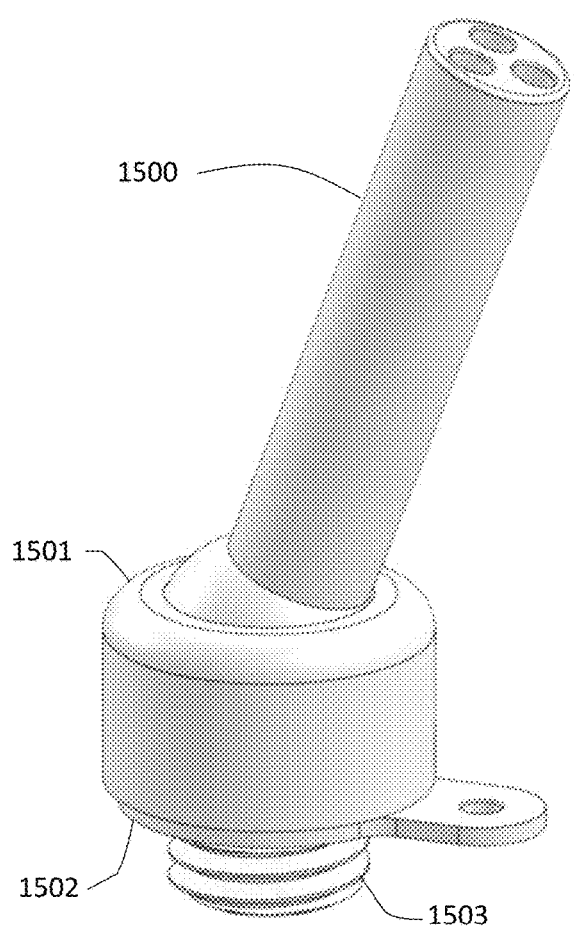
FIGS. 15A-15B depict a targeting system, as described herein, having a base with an in vivo portion.
Figure 15B:
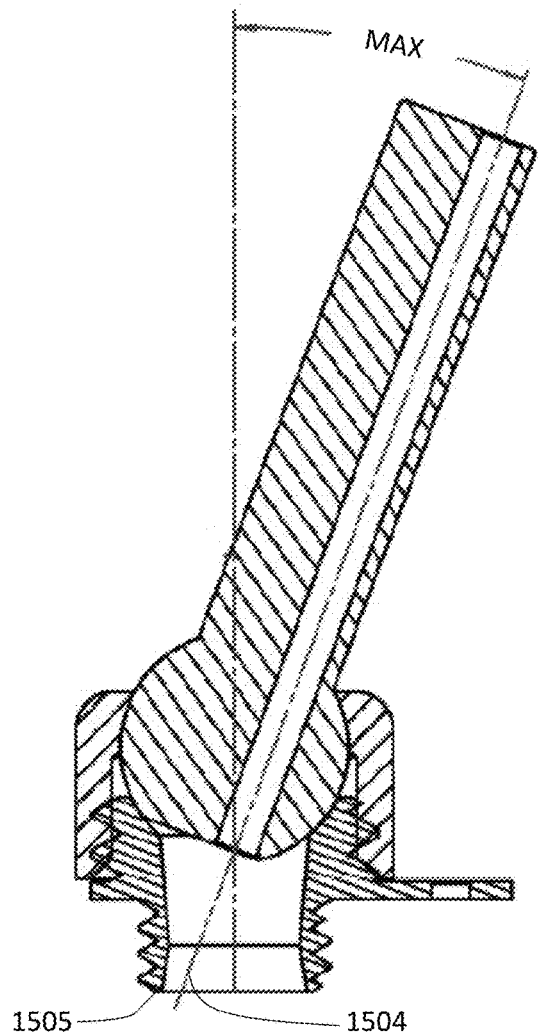

In comparison, the base of a targeting system may be configured to extend into the subject and substantially break the plane separating ex vivo from in vivo. A depiction of such a situation is provide in FIG. 15A and the corresponding cross section of FIG. 15B. This situation includes a turret (1500), a locking collar (1501) and a base (1502) wherein the base includes a treaded portion that, when attached to a tissue surface of the subject, extends into the subject (1503). Accordingly, the instantly described situation is not completely or substantially ex vivo as a portion of the base is positioned in vivo. A consequence of this configuration, which can be seen in the cross section of FIG. 15B, is that at angle adjustments approaching maximum ("MAX") the trajectory (1504) of one or more channels of the turret can be blocked by the in vivo edge (1505) of the base. In contrast, as can be seen in the cross section of FIG. 14C, in embodiments where the base is substantially or completely ex vivo, interference of any edge of the base with the trajectory of one or more channels is minimized.

In some instances, the base of a targeting system may, when the system is assembled and attached to a subject, remain substantially or completely ex vivo but the round end of the turret may protrude into the subject and thus be in vivo. In such instances, the amount that the rounded end of the turret that is in vivo when assembled may vary depending on the particular turret and base configuration.

In some instances, a targeting system may include a trajectory guide and a multicomponent turret-based system that is substantially ex vivo. In some instances, the trajectory guide of such a system may be configured with styles of such a length that, when the styles are inserted into the channels of the turret the trajectory guide remains substantially or completely ex vivo. In some instances, the trajectory guide of such a system may be configured with styles of such a length that, when the styles are inserted into the channels of the turret the styles of the trajectory guide exceed beyond the rounded end of the turret and are thus positions at least partially in vivo.

The base configured to receive the round end of the adjustable turret may also serve to attach the assembled multi-component device to a tissue surface of a subject. Any convenient means of attaching the base to the surface of the subject may be employed and the base may be configured and/or modified to allow for such varied methods of attachment. In some instances, e.g., as depicted in the embodiment of the base of FIG. 10, the base may include an attachment flange (1000) or a plurality of attachment flanges which may be arranged in any convenient orientation including but not limited to orthogonal to one or more walls of the base. The number of flanges on a base of the subject devices will vary and may include but is not limited to e.g., 1 or more, 2 or more, 3 or more, 4 or more, 5 or more, 6 or more, etc.

In some instances, the base may have a plurality of annular walls (1001) which collectively form a "socket" which receives the rounded end of the adjustable turret. The base may include threading on an external surface of the annular walls (1002) and a plurality of slots (1003) positioned between the annular walls. The configuration having slots between the treaded annular walls, e.g., as depicted in FIG. 10, allow for essentially uniform compression on the rounded end of the adjustable turret to be created when the locking collar is treaded to the base and tightened. While being dimensioned to receive the spherical end of the adjustable turret, the size of the base may vary. For example, in some instances, the area covered by the base may range from less than 1 $cm^2$ to 100 $cm^2$ or more including but not limited to e.g., 1 $cm^2$ to 100 $cm^2$, 1 $cm^2$ to 75 $cm^2$, 1 $cm^2$ to 50 $cm^2$, 1 $cm^2$ to 25 $cm^2$, 1 $cm^2$ to 20 $cm^2$, 1 $cm^2$ to 15 $cm^2$, 1 $cm^2$ to 10 $cm^2$, 1 $cm^2$ to 9 $cm^2$, 1 $cm^2$ to 8 $cm^2$, 1 $cm^2$ to 7 $cm^2$, 1 $cm^2$ to 6 $cm^2$, 1 $cm^2$ to 5 $cm^2$, 10 $cm^2$ to 100 $cm^2$, 25 $cm^2$ to 100 $cm^2$, 50 $cm^2$ to 100 $cm^2$, 75 $cm^2$ to 100 $cm^2$, etc.

In some instances, the device or system may further include a cap to cover the device or system and/or keep any openings free of debris when not in use. Useful caps include but are not limited to e.g., a cap configured to cover the distal end of the turret, a cap configured cover the base, etc. In some instances, owing to the removability of the turret from the base, e.g., by "snapping out" the turret from the base, the turret may be removed leaving an exposed hole through the center of the base. In some instances, the system or device may include a cap configured to fit on top of the base when the turret is removed to cover any exposed hole within the center of the base. One embodiment of a cap configured to cover the base when the turret is removed is depicted in FIG. 11. Caps as described herein may be held in place by any convenient means, including e.g., compression force, a fastener, etc. As such, a cap may or may not be threaded. For example, in some instances, a cap is configured with internal threading compatible with the external threading on the annular walls of the base such that the cap may be screwed into place, e.g., when the device is not in use.

As described in some detail above, various components of the devices and systems described herein may be symmetrical or asymmetrical. Symmetry of components of the device and systems includes internal symmetry and symmetry relative to another component, e.g., where two components are positioned or attached symmetrically.

In some instances, the presence of an asymmetry in a component of a device or system may provide a reference point during imaging to orient the image, i.e., provide a reference point to differentiate one side of an imaged trajectory guide from another side of the imaged trajectory guide. Any asymmetry in the system, e.g., that can be seen visually or that can be identified on a MRI-image, may be utilized in orienting one or more components of the system.

For example, in some instances, the turret may contain an asymmetry including but not limited to e.g., a groove or indentation, to serve as a reference point. As an example, in the embodiment of a turret depicted in FIG. 12, the turret is configured with a groove (arrow) in one position on the turret to serve as a reference point used to orient the turret and/or identify the particular channels of the turret. Other useful features that may serve as an asymmetry include but are not limited to e.g., flat sections, screw holes, screws, etc.).

Figure 13:
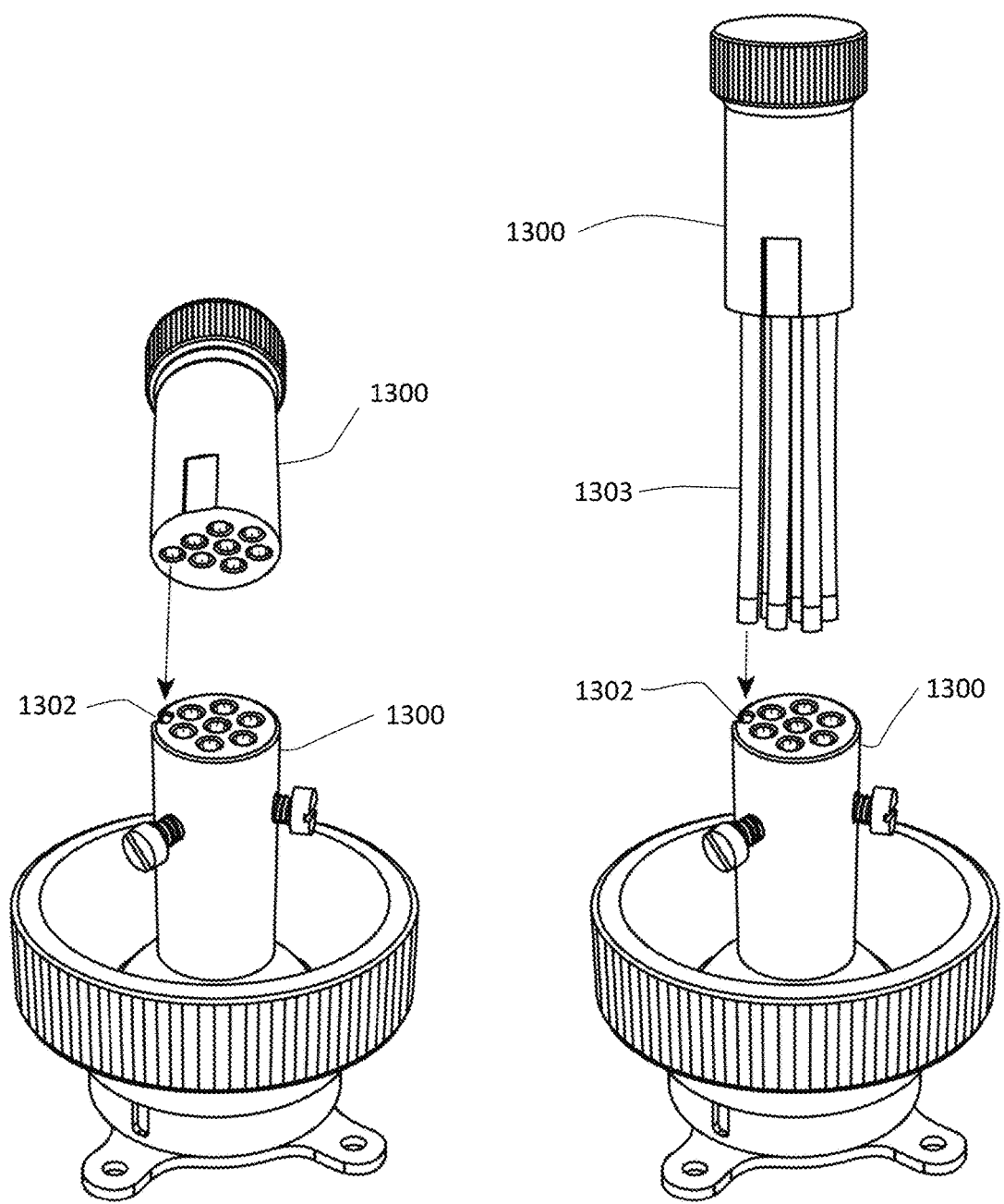
FIG. 13 depicts a trajectory guide and targeting device system according to an embodiment described herein.

In some instances, the styles of a trajectory guide may be arranged asymmetrically such that, when viewed on an MRI-imager the asymmetry may serve as a reference point and a means of indicating to a user or a computer to the orientation of the targeting guide. For example, in one embodiment, depicted in FIG. 13 the trajectory guide (1300) (pictured on the left without styles attached and on the right with styles attached) has an asymmetrical configuration of styles. All but one style of this asymmetric configuration corresponds to the symmetric channels of the adjustable turret (1301). The turret also contains an asymmetric groove (1302). In the embodiment depicted, the asymmetric style (1303) may be configured to align with the asymmetric groove (1302). Accordingly, when the styles of the trajectory guide are inserted into the channels and groove of the turret the asymmetric style provides orientation of the targeting system and identification of each channel of the turret using MRI imaging.

Systems of the instant disclosure may further include an MRI imager. As used herein the term "MRI imager" generally refers to any device that functions using the principles of nuclear magnetic resonance imaging that are well-known to the ordinary skilled artisan and include but are not limited to those devices commercially available in the relevant medical arts MRI.

Biomedical Systems

Aspects of the instant disclosure include targeted devices that may further include one or more biomedical systems for delivering a targeted therapy to a subject. The subject biomedical systems will include any suitable device for delivering or performing any of the therapeutic methods described above, provided the device or the operable portion thereof is able to be physically introduced through a channel of a targeting device as described herein.

In some instances, a biomedical system applied using a targeting device of the instant disclosure is a therapeutic delivery device, e.g., a drug delivery device. Any suitable drug delivery device may find use in the subject devices including but not limited to e.g., a needle, a cannula, an osmotic pump, a catheter, etc.

In some instances, a biomedical system applied using a targeting device of the instant disclosure is a therapy device for delivering electrical current or other energy (e.g., heat) to a desired area of a subject. Any suitable probe for therapeutic delivery may find use in the subject devices including but not limited to e.g., a heat probe, an electrode, etc.

In some instances, the biomedical device targeted through a channel of the subject targeting system may include a depth stop. As used herein, the term "depth stop" refers to any mechanism used to prevent the adverse and undesirable over-insertion of the biomedical device into the subject. In some instances, such depth stops may be configured of a sufficient diameter to prevent the biomedical device from proceeding into the subject when the depth stop contacts the adjustable turret of the targeting device.

In some instances, biomedical systems of the instant disclosure include an integrated system having a MRI-imaging unit a targeting device with a corresponding biomedical therapy device. In such systems, the MRI-imaging unit, and optionally the targeting and/or delivery device, may be communicably connected to a processing device, such as a processor.

Figure 16:
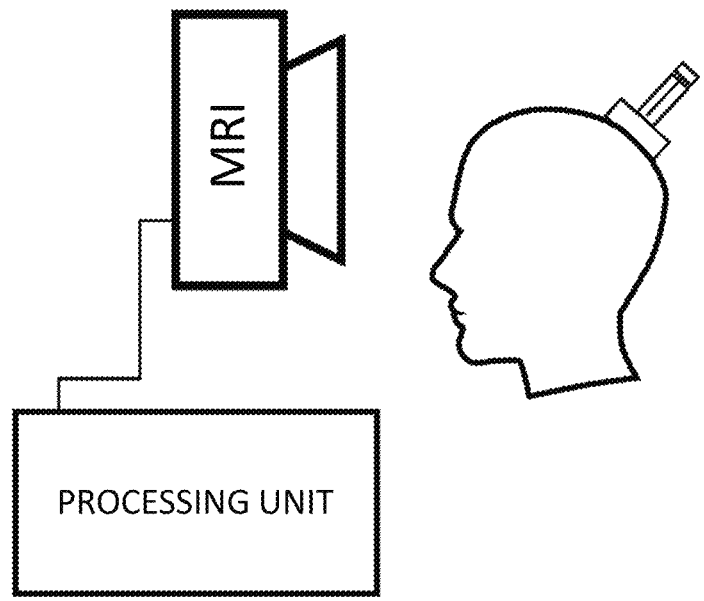
FIG. 16 depicts a targeting system as described herein.

For example, in the embodiment depicted in FIG. 16, a system of the instant disclosure may include a targeting device with a targeting guide in a positional relationship to an MRI-imager ("MRI") to allow the MRI-imager to image the targeting device, targeting guide and the desired region of treatment of the subject. The MRI-imager may further be connected to a processing unit configured to receive the images from the MRI-imager, process the images and output the results. In some instances, processing of the images may include determining the trajectory of one or more channels of the targeting device and displaying or otherwise reporting the result to a user. In some instances, the processor-connected MRI-imager outputs the MRI images of the trajectory guide but any determination of the trajectory is made manually.

Figure 17:
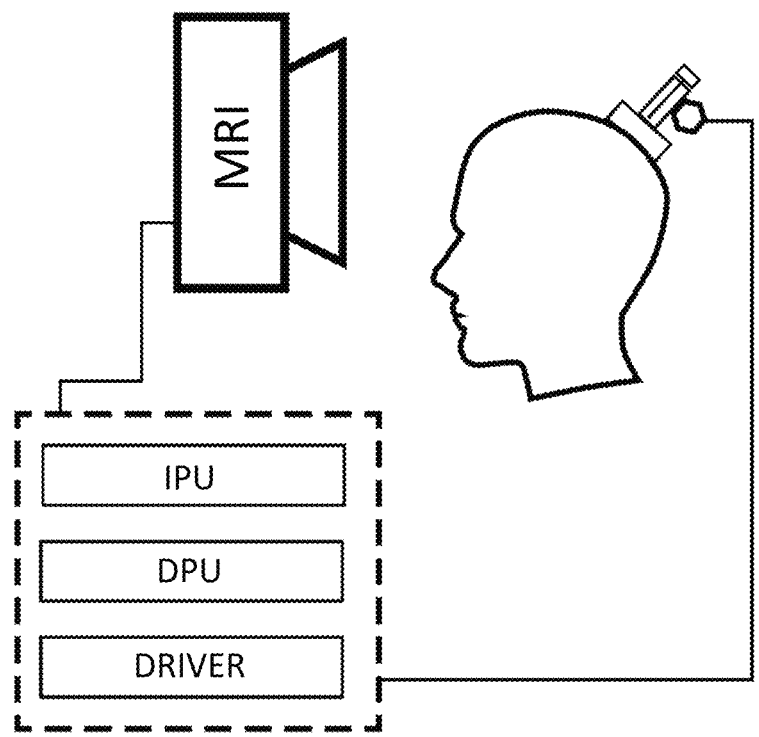
FIG. 17 depicts a targeting system as described herein.

The embodiment depicted in FIG. 17, extends the embodiment of FIG. 16, where the system further include a connection between the processing unit and the targeting device. A connection between the processor and the targeting device may be used for a variety of non-mutually exclusive purposes. For example, in some instances, the delivery of an agent, electrical current or other therapy may be computer controlled by the processor such that, upon proper targeting, the computer, with or without further user input, triggers delivery.

In some instances, the targeting adjustments of the targeting device may be computer controlled. For example, the targeting device may further include one or more computer controlled motors or actuators operably coupled to the adjustable turret such that targeting adjustments may be computer controlled. Computer controlled targeting adjustments may be dependent on user input defining the adjustment or the adjustment may be automated based on a computer calculated trajectory and adjustment. Whether the adjustment is manual or computer determined, the described systems will generally include at least a user input to define the target region of the subject.

The processor unit of FIG. 17, include an image processing unit (IPU) configured to receive the image from the MRI-imager, a data processing unit (DPU) configured to determine the trajectory from data received from the IPU, calculate the difference between the determined trajectory and a user inputted desired trajectory and signal any necessary adjustment. In some instances, a signaled necessary adjustment may be transferred to a computer driver ("DRIVER") that translates the signal to movement instructions such that either a user or motor/actuator driven components perform the necessary adjustment of the targeting device. The delivery of the therapy to the subject may also be user controlled or may be computer controlled e.g., by one or more drivers used to trigger a delivery signal.

Figure 18:
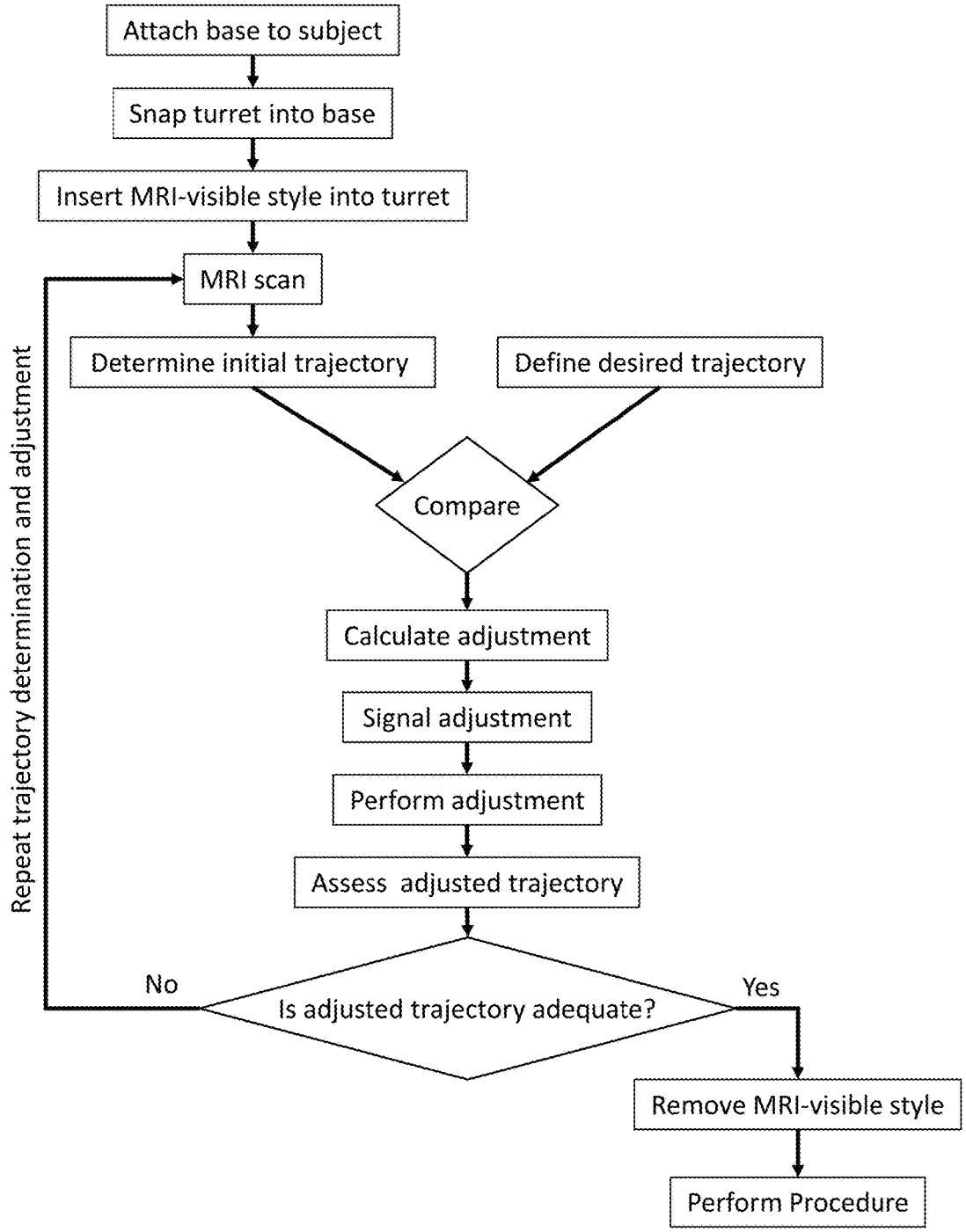
FIG. 18 provides a flowchart demonstrating the movement through a targeting system process as described herein.

The steps of a process for performing a herein disclosed method of targeting using a described system to deliver a procedure to a subject is outlined in FIG. 18. Essentially, using a herein described apparatus, the base of a targeting device is attached to a subject and the turret is snapped into the base. A targeting guide is used to insert an MRI-visible style into the turret and an MRI scan is performed. From the MRI scan the initial trajectory is determined and the system compares the determined trajectory to a user inputted desired trajectory. The system calculates an adjustment based on the comparison and signals the adjustment to the user of a component of the system configured to make the adjustment. The adjustment is performed, either by the user or the system and the adjusted trajectory is assessed. If the adjusted trajectory is sufficient the MRI-visible style may be removed and the treatment may be delivered. If the adjusted trajectory is insufficient, the system may loop back to the MRI scan and may repeat the trajectory determination and adjustment. As noted, the individual processes outlined in FIG. 18 may, where appropriate be computer controlled.

In some instances, the components of the systems as described herein may be connected by a wired data connection. Any suitable and appropriate wired data connection may find use in connecting the components of the described systems, e.g., as described herein, including but not limited to e.g., commercially available cables such as a USB cable, a coaxial cable, a serial cable, a C2G or Cat2 cable, a Cat5/Cat5e/Cat6/Cat6a cable, a Token Ring Cable (Cat4), a VGA cable, a HDMI cable, a RCA cable, an optical fiber cable, and the like. In some instances, e.g., where data security is less of a concern, wireless data connections may be employed including but not limited to e.g., radio frequency connections (e.g., PAN/LAN/MAN/WAN wireless networking, UHF radio connections, etc.), an infrared data transmission connection, wireless optical data connections, and the like.

The devices and systems of the instant disclosure may further include a "memory" that is capable of storing information such that it is accessible and retrievable at a later date by a computer. Any convenient data storage structure may be chosen, based on the means used to access the stored information. In certain aspects, the information may be stored in a "permanent memory" (i.e. memory that is not erased by termination of the electrical supply to a computer or processor) or "non-permanent memory". Computer harddrive, CD-ROM, floppy disk, portable flash drive and DVD are all examples of permanent memory. Random Access Memory (RAM) is an example of non-permanent memory. A file in permanent memory may be editable and re-writable.

Substantially any circuitry can be configured to a functional arrangement within the devices and systems for performing the methods disclosed herein. The hardware architecture of such circuitry, including e.g., a specifically configured computer, is well known by a person skilled in the art, and can comprise hardware components including one or more processors (CPU), a random-access memory (RAM), a read-only memory (ROM), an internal or external data storage medium (e.g., hard disk drive). Such circuitry can also comprise one or more graphic boards for processing and outputting graphical information to display means. The above components can be suitably interconnected via a bus within the circuitry, e.g., inside a specific-use computer. The circuitry can further comprise suitable interfaces for communicating with general-purpose external components such as a monitor, keyboard, mouse, network, etc. In some embodiments, the circuitry can be capable of parallel processing or can be part of a network configured for parallel or distributive computing to increase the processing power for the present methods and programs. In some embodiments, the program code read out from the storage medium can be written into a memory provided in an expanded board inserted in the circuitry, or an expanded unit connected to the circuitry, and a CPU or the like provided in the expanded board or expanded unit can actually perform a part or all of the operations according to the instructions of the programming, so as to accomplish the functions described.

In addition to the components of the devices and systems of the instant disclosure, e.g., as described above, systems of the disclosure may include a number of additional components, such as data output devices, e.g., monitors and/or speakers, data input devices, e.g., interface ports, keyboards, etc., actuatable components, power sources, etc.

Computer Readable Media

The instant disclosure includes computer readable medium, including non-transitory computer readable medium, which stores instructions for methods described herein. Aspects of the instant disclosure include computer readable medium storing instructions that, when executed by a computing device, cause the computing device to perform one or more steps of a method as described herein.

In certain embodiments, instructions in accordance with the methods described herein can be coded onto a computer-readable medium in the form of "programming", where the term "computer readable medium" as used herein refers to any storage or transmission medium that participates in providing instructions and/or data to a computer for execution and/or processing. Examples of storage media include a floppy disk, hard disk, optical disk, magneto-optical disk, CD-ROM, CD-ft magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer.

The computer-implemented method described herein can be executed using programming that can be written in one or more of any number of computer programming languages. Such languages include, for example, Java (Sun Microsystems, Inc., Santa Clara, Calif.), Visual Basic (Microsoft Corp., Redmond, Wash.), and C++ (AT&T Corp., Bedminster, N.J.), as well as any many others.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A trajectory guide for magnetic resonance imaging (MRI)-assisted targeting of a desired area of a subject, comprising:
   a solid support comprising a flat surface; and
   a plurality of MRI-visible styles each comprising a lumen comprising a contrast agent, wherein each MRI-visible style of the plurality is affixed at one end to the flat surface and dimensioned for insertion into each channel of an adjustable turret comprising a plurality of channels, the adjustable turret affixed to a tissue surface of a subject thereby allowing targeting of each channel by visualizing the trajectory of each inserted MRI-visible style using an MRI imager.

2. The trajectory guide of claim 1, wherein the plurality of MRI-visible styles comprises two or more styles that are affixed symmetrically to the flat surface with respect to the geometric center of the flat surface.

3. The trajectory guide of claim 1, wherein the plurality of MRI-visible styles comprises at least one style that is affixed asymmetrically to the flat surface with respect to one or more styles of the plurality.

4. The trajectory guide of claim 1, wherein the plurality of MRI-visible styles are affixed perpendicular to the flat surface.

5. The trajectory guide of claim 1, wherein the plurality of MRI-visible styles are affixed at a flared angle to the flat surface.

6. The trajectory guide of claim 1, wherein the solid support comprises an opening, opposite the flat surface, adjoining a void within the solid support that is contiguous with the lumens of the MRI-visible styles thereby allowing access to the void and the lumens.

7. The trajectory guide of claim 6, further comprising a cap for closing the opening.

8. The trajectory guide of claim 7, wherein the cap and the opening comprise compatible threading.

9. The trajectory guide of claim 1, wherein the contrast agent comprises gadolinium.

10. An adjustable targeting system, the system comprising:
    an adjustable turret comprising a distal end, a spherical end and a plurality of channels running from the distal end to the spherical end; and
    a base, comprising:
        a plurality of annular walls forming a socket dimensioned to receive the spherical end;
        a plurality of slots positioned between the plurality of annular walls; and
        a flange orthogonal to at least one of the annular walls for affixing the base to a tissue surface of a subject, wherein the channels are configured for insertion of a plurality of MRI-visible styles affixed at one end to a flat surface of a solid support of a trajectory guide into the channels.

11. The system of claim 10, further comprising a locking collar comprising threading on an internal surface compatible with threading on the external surface of the base, wherein turning the locking collar a first direction compresses the spherical end to lock the adjustable turret in a desired trajectory and turning the locking collar a second direction decompresses the spherical end to allow for retargeting of the trajectory of the adjustable turret, and wherein turning the locking collar the first direction compresses the spherical end between the base and the locking collar to lock the adjustable turret in a desired trajectory.

12. The system of claim 10, further comprising a locking collar comprising threading on an internal surface compatible with threading on the external surface of the base, wherein turning the locking collar a first direction compresses the spherical end to lock the adjustable turret in a desired trajectory and turning the locking collar a second direction decompresses the spherical end to allow for retargeting of the trajectory of the adjustable turret, and wherein turning the locking collar the first direction compresses the spherical end between the plurality of annular walls of the socket to lock the adjustable turret in a desired trajectory.

13. The system of claim 10, wherein the adjustable targeting system is configured such that when affixed to the tissue surface of the subject the base and the locking collar are ex vivo.

14. The system of claim 10, wherein the adjustable targeting system is configured such that when affixed to the tissue surface of the subject the adjustable turret is ex vivo.

15. The system of claim 10, wherein the spherical end comprises a flat portion opposite the distal end that comprises openings to the one or more channels.

16. The system of claim 15, wherein the spherical end and the flat portion are dimensioned such that, when inserted into the socket, the flat portion is flush with the bottom surface of the base.

17. The system of claim 11, wherein the locking collar comprises a knurled external surface to provide grip.

18. The system of claim 10, wherein the base comprises a plurality of flanges orthogonal to at least one of the annular walls.

19. The system of claim 10, further comprising a trajectory guide comprising:
    a solid support comprising a flat surface; and
    a plurality of MRI-visible styles each comprising a lumen comprising a contrast agent, wherein the MRI-visible styles are affixed at one end to the flat surface and dimensioned for insertion into RA the channels of the adjustable turret affixed to a tissue surface of the subject thereby allowing targeting of the channels by visualizing the trajectory of the inserted MRI-visible styles using an MRI imager.

20. The system of claim 19, wherein the system further comprises an MRI imager positioned to image the MRI-visible styles of the trajectory guide when the MRI-visible styles are inserted into the channels of the adjustable turret.

21. An adjustable targeted delivery system, the system comprising:
    an adjustable targeting system according to claim 10; and
    a delivery device or electrode dimensioned for insertion into a channel of the plurality of channels of the adjustable turret.

22. The system of claim 21, wherein the delivery device or electrode comprises a depth stop positioned at a point along the length of the delivery device or electrode to prevent inserting the delivery device into the channel past said point.

23. An automated adjustable targeting system, the system comprising:
    an adjustable targeting system according to claim 10;
    an actuator connected to the adjustable turret and controlled by a processor programmed with instructions that, when executed by the processor, cause the processor to:
        determine the trajectory of a channel of the adjustable turret based on a received magnetic resonance image (MRI) of a trajectory guide MRI-visible style inserted within the channel;
        compare the determined trajectory to a desired user input trajectory;
        calculate an adjustment of the adjustable turret necessary to align the determined trajectory with the desired user input trajectory based on the comparing; and
        trigger the actuator to execute the adjustment thereby aligning the determined trajectory with the desired user input trajectory.

24. The adjustable targeting system of claim 10, wherein the plurality of channels comprises at least two channels that are parallel.

25. The adjustable targeting system of claim 10, wherein the plurality of channels comprises at least two channels that are nonparallel.

\* \* \* \* \*